United States Patent
Bjurbo et al.

(10) Patent No.: US 12,233,254 B2
(45) Date of Patent: Feb. 25, 2025

(54) SYSTEM AND METHOD FOR MUSCLE STIMULATION AND/OR IMPEDANCE MEASUREMENT TO VERIFY PROPER TUBE PLACEMENT

(71) Applicant: Avent, Inc., Alpharetta, GA (US)

(72) Inventors: Karl Thomas Bjurbo, Cumming, GA (US); Eric A. Schepis, Alpharetta, GA (US); James F. Tassitano, Marietta, GA (US)

(73) Assignee: Avent, Inc., Alpharetta, GA (US)

( * ) Notice: Subject to any disclaimer, the term of this patent is extended or adjusted under 35 U.S.C. 154(b) by 5 days.

(21) Appl. No.: 16/881,223

(22) Filed: May 22, 2020

(65) Prior Publication Data
US 2021/0361934 A1    Nov. 25, 2021

(51) Int. Cl.
| | |
|---|---|
| *A61N 1/05* | (2006.01) |
| *A61M 25/01* | (2006.01) |
| *A61N 1/372* | (2006.01) |
| *A61N 1/375* | (2006.01) |
| *A61N 1/378* | (2006.01) |
| *A61N 1/08* | (2006.01) |

(52) U.S. Cl.
CPC ....... *A61N 1/0507* (2013.01); *A61M 25/0105* (2013.01); *A61N 1/37247* (2013.01); *A61N 1/37258* (2013.01); *A61N 1/3754* (2013.01); *A61N 1/378* (2013.01); *A61M 2025/0166* (2013.01); *A61M 2210/10* (2013.01); *A61N 2001/083* (2013.01)

(58) Field of Classification Search
CPC ............ A61N 1/0507; A61N 2001/083; A61N 1/37247; A61N 1/37258; A61N 1/3754; A61N 1/378; A61M 25/0105; A61M 2025/0166; A61M 2210/10
See application file for complete search history.

(56) References Cited

U.S. PATENT DOCUMENTS

| | | | |
|---|---|---|---|
| 4,921,481 | A | 5/1990 | Danis et al. |
| 5,556,425 | A | 9/1996 | Hewson et al. |

(Continued)

FOREIGN PATENT DOCUMENTS

| | | |
|---|---|---|
| WO | WO 97/19667 A1 | 6/1997 |
| WO | WO 02/26320 A1 | 4/2002 |

(Continued)

OTHER PUBLICATIONS

International Search Report and Written Opinion for PCT/US2021/031755, dated Aug. 9, 2021, 14 pages.

*Primary Examiner* — Deborah L Malamud
(74) *Attorney, Agent, or Firm* — Meunier Carlin & Curfman LLC

(57) ABSTRACT

A tubing assembly for use with an electronic catheter guidance systems is provided and includes a catheter and a stimulation electrode assembly, and an electrical connection for delivering a stimulation waveform to the stimulation electrode assembly. The catheter extends in a longitudinal direction and has a proximal end and a distal end that define a lumen therebetween. Further, the catheter is configured for placement within a patient's digestive tract. The stimulation electrode assembly is configured to deliver an electrical stimulation to tissue. A catheter guidance system and method for accurately placing a catheter in the digestive tract are also provided.

17 Claims, 14 Drawing Sheets

(56) References Cited

U.S. PATENT DOCUMENTS

| | | |
|---|---|---|
| 6,584,348 B2 | 6/2003 | Glukhovsky |
| 6,754,536 B2 | 6/2004 | Swoyer et al. |
| 7,734,351 B2 | 6/2010 | Testermam et al. |
| 8,032,222 B2 | 10/2011 | Loushin et al. |
| 8,092,433 B2 | 1/2012 | Hamdy |
| 8,275,460 B2 | 9/2012 | Loushin et al. |
| 8,280,498 B2 | 10/2012 | Jalde |
| 8,285,399 B2 | 10/2012 | Van Bommel et al. |
| 8,355,801 B2 | 1/2013 | O'Sullivan |
| 8,448,636 B2 | 5/2013 | Singh |
| 8,613,702 B2 | 12/2013 | Feer et al. |
| 8,863,742 B2 | 10/2014 | Blomquist et al. |
| 8,909,315 B2 | 12/2014 | Förtsch et al. |
| 9,037,245 B2 | 5/2015 | Sharma et al. |
| 9,055,880 B2 | 6/2015 | Jalde et al. |
| 9,446,228 B2 | 9/2016 | Libbus et al. |
| 9,474,468 B2 | 10/2016 | Sinderby et al. |
| 9,486,157 B2 | 11/2016 | Wik |
| 9,675,265 B2 | 6/2017 | Weekamp et al. |
| 9,713,579 B2 | 7/2017 | Elia et al. |
| 10,058,669 B2 | 8/2018 | Razavi et al. |
| 10,143,416 B2 | 12/2018 | Bhargava |
| 10,219,747 B2 | 5/2019 | Meftah et al. |
| 10,278,616 B2 | 5/2019 | Schwartz et al. |
| 10,321,867 B2 | 6/2019 | Mabary et al. |
| 10,384,052 B2 | 8/2019 | Tal et al. |
| 10,398,630 B2 | 9/2019 | Azzolini et al. |
| 10,426,955 B2 | 10/2019 | Sharma et al. |
| 10,548,816 B2 | 2/2020 | Elia et al. |
| 2005/0159659 A1 | 7/2005 | Sawan et al. |
| 2006/0116564 A1 | 6/2006 | Mintchev et al. |
| 2008/0077043 A1 | 3/2008 | Malbrain et al. |
| 2008/0319504 A1 | 12/2008 | Loushin et al. |
| 2010/0106207 A1* | 4/2010 | Dobak, III ............ A61K 45/06 607/3 |
| 2015/0157820 A1* | 6/2015 | Razavi ............ A61M 16/0488 128/200.26 |
| 2015/0343211 A1* | 12/2015 | Tal ........................ A61N 1/3727 607/40 |
| 2015/0374982 A1* | 12/2015 | Tal ........................ A61N 1/0517 607/40 |
| 2016/0029998 A1* | 2/2016 | Brister ................. A61B 8/0833 600/424 |
| 2017/0347921 A1* | 12/2017 | Haber ................. A61N 1/36114 |
| 2018/0078195 A1 | 3/2018 | Sutaria et al. |
| 2019/0038894 A1 | 2/2019 | Bassi et al. |
| 2019/0059782 A1 | 2/2019 | Valderrabano et al. |
| 2019/0083725 A1 | 3/2019 | Elia et al. |
| 2019/0313970 A1 | 10/2019 | Elia et al. |
| 2019/0365276 A1 | 12/2019 | Vaezi et al. |
| 2020/0306141 A1 | 10/2020 | Meadows et al. |
| 2021/0030629 A1 | 2/2021 | McMichael et al. |

FOREIGN PATENT DOCUMENTS

| | | | |
|---|---|---|---|
| WO | WO 2014/105759 A1 | 7/2014 | |
| WO | WO2016187456 * | 11/2016 | ............. A61B 5/053 |
| WO | WO-2016187456 A1 * | 11/2016 | ........... A61B 5/0536 |
| WO | WO 2019/091991 A1 | 5/2019 | |
| WO | WO 2020/069171 A1 | 4/2020 | |

\* cited by examiner

SYSTEM AND METHOD FOR MUSCLE STIMULATION AND/OR IMPEDANCE MEASUREMENT TO VERIFY PROPER TUBE PLACEMENT

BACKGROUND OF THE INVENTION

Physicians and other health care providers frequently use catheters to treat patients. Known catheters include a tube which is inserted into the human body. Certain catheters are inserted through the patient's nose or mouth for treating the digestive or gastrointestinal tract. These catheters, sometimes referred to as enteral catheters, typically include feeding tubes. The feeding tube lies in the stomach or intestines, and a feeding bag delivers liquid nutrient, liquid medicine or a combination of the two to the patient.

When using such catheters, it is important to place the end of the catheter at the proper location within the human body. Erroneous placement of the catheter tip may injure or harm the patient. For example, if the health care provider erroneously places an enteral catheter into the patient's trachea, lungs, or other anatomical regions of the respiratory system or airway rather than through the esophagus and to the stomach to reach the desired location in the digestive tract for delivering nutrients or medicine, liquid may be introduced into the lungs with harmful, and even fatal, consequences. In particular, the esophagus of the digestive tract and the trachea of the respiratory system are in close proximity to each other and are blind to the health care provider during catheter placement, which creates a dangerous risk for erroneous catheter placement.

In some cases, health care providers use X-ray machines to gather information about the location of the catheters within the body. There are several disadvantages with using X-ray machines. For example, X-ray machines are relatively large and heavy, consume a relatively large amount of energy and may expose the patient to a relatively high degree of radiation. Also, these machines are typically not readily accessible for use because, due to their size, they are usually installed in a special X-ray room. This room can be far away from the patient's room. Therefore, health care providers may find it inconvenient to use these machines for their catheter procedures. In addition, using X-ray technology is expensive and is a time-consuming task that can create unnecessary delays in delivering critical nutrients to the patient.

Accordingly, there is a need to overcome each of these disadvantages.

SUMMARY OF THE INVENTION

Objects and advantages of the invention will be set forth in part in the following description, or may be obvious from the description, or may be learned through practice of the invention.

In one particular embodiment, the present invention is directed to a tubing assembly. The tubing assembly includes a catheter having a proximal end and a distal end and extending in a longitudinal direction, wherein the proximal end and the distal end define a lumen therebetween, and wherein the catheter is configured for placement within a digestive tract of a patient; a stimulation electrode assembly, wherein the stimulation electrode assembly is configured to deliver an electrical stimulation to tissue; and an electrical connection for delivering a stimulation waveform to the stimulation electrode assembly.

In another embodiment, the stimulation electrode assembly can include an anode and a cathode, wherein the anode and the cathode are disposed on an outer wall of the distal end of the catheter.

In still another embodiment, the stimulation electrode assembly can include a first electrode disposed on an outer wall of the catheter and a second electrode configured for placement on a surface of skin.

In yet another embodiment, the tubing assembly can also include a recording electrode assembly. The recording electrode assembly can include an active recording electrode, an inactive recording electrode, and a reference electrode. Further, the active recording electrode, the inactive recording electrode, and the reference electrode can be disposed on an outer wall of the distal end of the catheter. Alternatively, the active recording electrode, the inactive recording electrode, and the reference electrode can be configured for placement on a surface of skin.

In one more embodiment, the recording electrode assembly can be configured to monitor for electrical activity elicited by the tissue in response to the stimulation waveform and communicate the electrical activity elicited by the tissue to a processor in real-time.

In an additional embodiment, the stimulation electrode assembly can be configured for a wired connection or a wireless connection to the processor. Further, the wired connection can include a wire or a printed conduit.

In another particular embodiment, the present invention is directed to a catheter guidance system. The catheter guidance system includes (a) a processor; (b) a power source; (c) a stimulator; and (d) a tubing assembly. Further, the tubing assembly includes a catheter having a proximal end and a distal end and extending in a longitudinal direction, wherein the proximal end and the distal end define a lumen therebetween; a stimulation electrode assembly, wherein the stimulation electrode assembly is configured to deliver an electrical stimulation to tissue; and a recording electrode assembly, wherein the recording electrode assembly is configured to monitor for electrical activity elicited by the tissue in response to the stimulation waveform, further wherein the recording electrode assembly communicates the electrical activity elicited by the tissue to the processor in real-time; wherein the catheter guidance system alerts a user as to correct placement of the catheter in a digestive tract of a patient or alerts the user as to incorrect placement of the catheter in a respiratory tract of the patient.

In one embodiment, the system can also include a display device, wherein the display device is coupled to the processor and displays a graph of the electrical activity elicited by the tissue and communicated to the processor by the recording electrode assembly.

In still another embodiment, the system can also include a memory device storing instructions which, when executed by the processor, cause the processor to (i) interpret the electrical activity elicited by the tissue and communicated by the recording electrode assembly and (ii) cause the catheter guidance system to alert the user as to correct placement of the catheter in the digestive tract of the patient or alert the user as to incorrect placement of the catheter in the respiratory tract of the patient based on the interpretation of the electrical activity elicited by the tissue.

In yet another embodiment, the stimulation electrode assembly can include an anode and a cathode, wherein the anode and the cathode are disposed on an outer wall of the distal end of the catheter.

In one more embodiment, the stimulation electrode assembly can include first electrode disposed on an outer wall of the catheter and a second electrode configured for placement on a surface of skin.

In an additional embodiment, the recording electrode assembly can include an active recording electrode, an inactive recording electrode, and a reference electrode. Further, the active recording electrode, the inactive recording electrode, and the reference electrode can be disposed on an outer wall of the distal end of the catheter. Alternatively, the active recording electrode, the inactive recording electrode, and the reference electrode can be configured for placement on a surface of skin.

In one more embodiment of the present invention, a method for determining if a catheter is placed within a digestive tract of a body of a patient is provided. The method includes (a) inserting a distal end of a tubing assembly into an orifice of the body, wherein the tubing assembly comprises: the catheter, wherein the catheter has a proximal end and a distal end and extends in a longitudinal direction, wherein the proximal end and the distal end define a lumen therebetween; a stimulation electrode assembly; and a recording electrode assembly; (b) electrically connecting the stimulation electrode assembly to a stimulator and the recording electrode assembly to a processor; (c) generating a stimulation waveform via the stimulator; (d) delivering the stimulation waveform to tissue via the stimulation electrode assembly as the catheter is advanced inside the body in a direction away from the orifice; (e) activating the recording electrode assembly, wherein the recording electrode assembly monitors for electrical activity elicited by the tissue in response to the stimulation waveform, further wherein the recording electrode assembly communicates the electrical activity elicited by the tissue to the processor in real-time; and (f) observing a graph of the electrical activity on a display device coupled to the processor, wherein the display device alerts a user as to correct placement of the catheter in the digestive tract of the patient or alerts the user as to incorrect placement of the catheter in a respiratory tract of the patient.

In another embodiment, a memory device stores instructions which, when executed by the processor, can cause the processor to (i) interpret the electrical activity elicited by the tissue and communicated by the recording electrode assembly and (ii) cause the display device to communicate whether or not the catheter is placed within the digestive tract of the patient based on the interpretation of the electrical activity elicited by the tissue.

In still another embodiment, if the electrical activity elicited by the tissue is in the form of one or more evoked potentials, then it can be confirmed that the catheter is placed in the digestive tract, and if the electrical activity elicited by the tissue is not in the form of one or more evoked potentials, then the catheter is not placed in the digestive tract.

In yet another embodiment, the system can monitor for electrical activity elicited by the tissue by measuring an impedance level of tissue via one or more electrical contacts in the stimulation electrode assembly or the recording electrode assembly, wherein a first level of impedance indicates that the catheter is placed in the digestive tract and a second level of impedance indicates that the catheter is not placed in the digestive tract.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Figure 1:
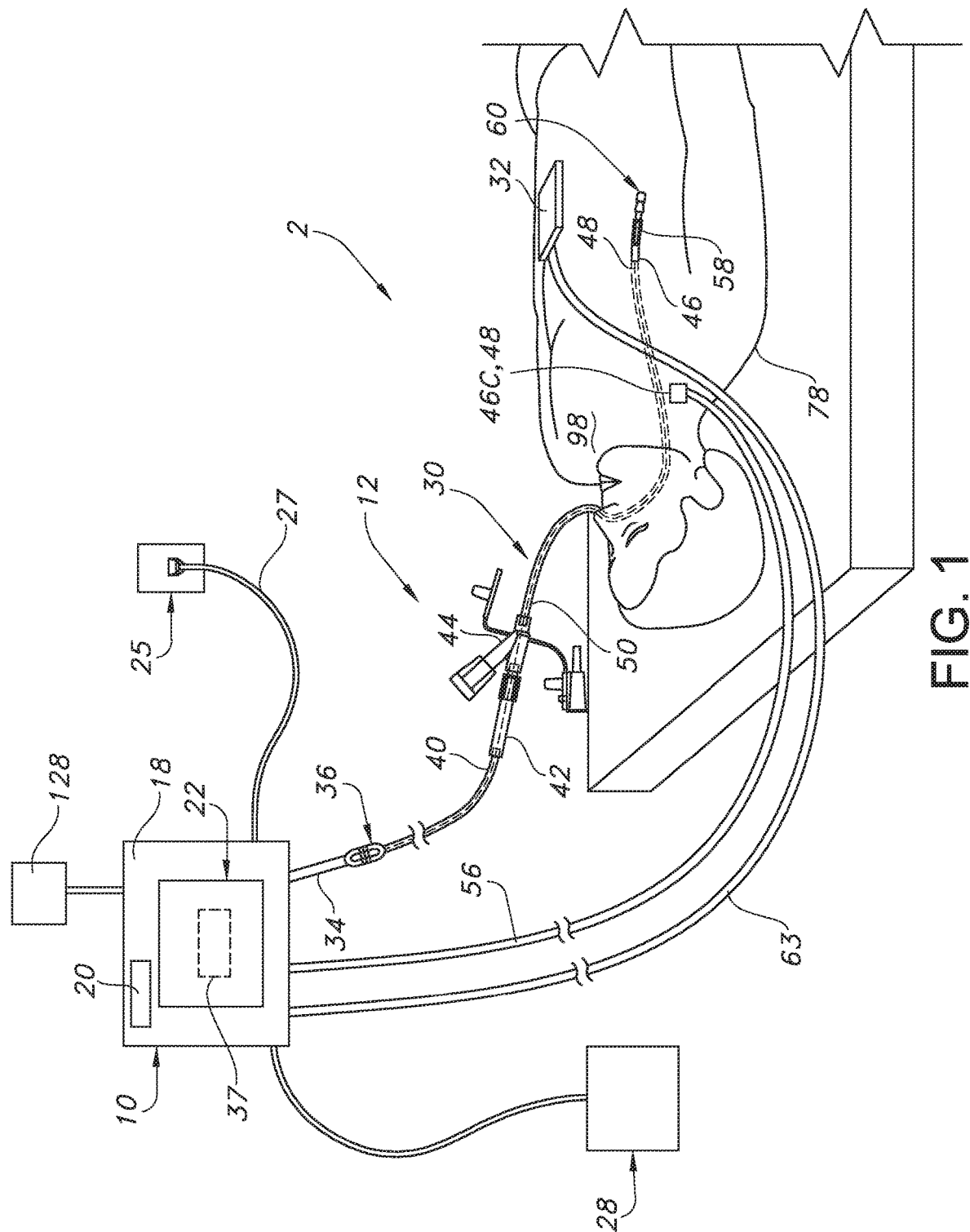
FIG. 1 is a perspective view of a catheter guidance system contemplated by the present invention illustrating the display device and the electronic catheter unit as it is being positioned within a patient in one embodiment of the present invention.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the terms "about," "approximately," or "generally," when used to modify a value, indicates that the value can be raised or lowered by 5% and remain within the disclosed embodiment. Further, when a plurality of ranges are provided, any combination of a minimum value and a maximum value described in the plurality of ranges are contemplated by the present invention. For example, if ranges of "from about 20% to about 80%" and "from about 30% to about 70%" are described, a range of "from about 20% to about 70%" or a range of "from about 30% to about 80%" are also contemplated by the present invention.

Generally speaking, the present invention is directed to a tubing assembly that includes a catheter having a proximal end and a distal end and extending in a longitudinal direction, where the proximal end and the distal end define a lumen therebetween. Further, the catheter is configured for placement within a digestive tract of a patient. The tubing assembly also includes a stimulation electrode assembly that is configured to deliver an electrical stimulation to tissue (e.g., esophageal tissue such as striated muscle or tissue in the trachea such as cartilage, connective tissue, and the trachealis muscle), as well as an electrical connection for delivering a stimulation waveform to the stimulation electrode assembly. A catheter guidance system and method for accurately placing a catheter in the digestive tract are also provided.

In addition to a stimulation electrode assembly, the tubing assembly contemplated by the present invention can also include a recording electrode assembly. The recording electrode assembly is configured to monitor for electrical activity elicited by the tissue in response to the stimulation waveform and communicate the electrical activity elicited by the tissue to a processor in real-time. For example, if the electrical activity elicited by the tissue in response to a stimulation waveform (e.g., a monophasic or biphasic square wave pulse) is in the form of one or more evoked potentials, then it can be confirmed that the catheter has been placed or inserted into the digestive tract. Meanwhile, if the electrical activity elicited by the tissue is not in the form of one or more evoked potentials, then it can be confirmed that the catheter is not placed in the digestive tract. Alternatively, if the electrical activity elicited by the tissue is monitored by measuring the impedance of the tissue in response to a stimulation waveform (e.g., an electrical noise signal, a single frequency waveform, multiple frequency waveforms superimposed on top of one another, etc.), a first level of impedance can indicate that the catheter is placed in the digestive tract, while a second level of impedance can indicated that the catheter is not placed in the digestive tract. The present inventors have found that the tubing assembly, catheter guidance system, and method described in more detail herein allow for the electrical activity elicited by tissue in response to a stimulation waveform delivered by the stimulation electrode assembly and captured in real-time via the recording electrode assembly can be used to determine if the distal end of the catheter is accurately placed within the digestive tract (e.g., the epiglottis, esophagus, stomach, intestines, etc.) rather than erroneously placed within the respiratory system (e.g., the trachea, bronchi, lungs, etc.), where such placement could be harmful and even fatal to a patient. Further, the present inventors have found that because the recording electrode assembly can obtain measurements and communicate those measurements to processor and ultimately a display device or other communication device (e.g., a phone, pager, etc.) in real time, the correct placement of the catheter can be confirmed within seconds of a catheter placement procedure, which can save valuable time, resources, and cost while at the same time limit patient risk in the event of the erroneous placement of the catheter.

Specifically, the present inventors have found that capturing and monitoring electrical activity elicited by tissue at a distal end of a catheter in response to a stimulation waveform in real-time, where the catheter is to be placed in a predetermined location along the digestive tract (e.g., esophagus, stomach, intestines, etc.), which is facilitated by the stimulation electrode assembly and the recording electrode assembly of the catheter guidance system of the present invention, allows for the efficient and accurate placement of the catheter within the digestive tract at a low cost. For instance, the recording electrode assembly of the tubing assembly can capture data associated with electrical activity elicited by tissue in response to stimulation in the form an electrical pulse waveform or random noise signal waveform within the catheter as it is being directed by a health care provider in to the body of a patient, where the recorded electrical activity (e.g., in the form of evoked potentials, impedance of tissue measured between electrical contacts, etc.) can then be transmitted to a display device via a processor. The health care provider can then view the electrical activity elicited by the tissue on the display device to determine if the catheter has been accurately placed in the digestive tract or erroneously placed in an anatomical region of the respiratory system (e.g., the trachea, bronchi, lungs, etc.). Alternatively or additionally, a memory device that can include machine readable instructions and one or more computer programs (which, for example, may include a plurality of algorithms) can be used by the processor to process the data from the recording electrode assembly, where the display device can then indicate the catheter information to the health care provider in the form of a signal as to whether the catheter is accurately placed in the digestive tract or erroneously placed within, for instance, a portion of the respiratory system. For example, a green check mark or the word "Yes" can be displayed on the screen to indicate accurate placement of the catheter within the digestive or gastrointestinal tract, while a red circle with a diagonal line through it, an "X", or the word "No" can be displayed on the screen for erroneous placement, such as placement within the respiratory system.

The various features of the catheter guidance system are discussed in detail below.

Referring now to the drawings, in an embodiment illustrated in FIGS. 1-4, the catheter guidance system 2 contemplated by the present invention includes: (a) an apparatus 10 having a housing 18 which supports a controller or processor 20 and a display device 22; (b) a power cord 27 that couples the apparatus 10 to a power source 25; (c) a printer 28 coupled to the apparatus 10 for printing out paper having graphics which indicate catheter location information; (d) an optional non-invasive movable receiver-transmitter or transceiver 32 electronically coupled to the processor 20 by a wire, cable, signal data connection or signal carrier 63; and (e) an invasive electronic catheter unit 12 in communication with and operatively coupled to the apparatus 10 by a wire, cable, cord or electrical extension 34, which, in turn, is operatively coupled to the processor 20, where the electronic catheter unit 12 includes a tubing assembly 14 that includes a catheter 50; a stimulation electrode assembly 46; a recording electrode assembly 48; a stimulator 128; and an optional signal generator 58 when the system 2 includes the optional non-invasive movable receiver-transmitter or transceiver 32.

Figure 2:
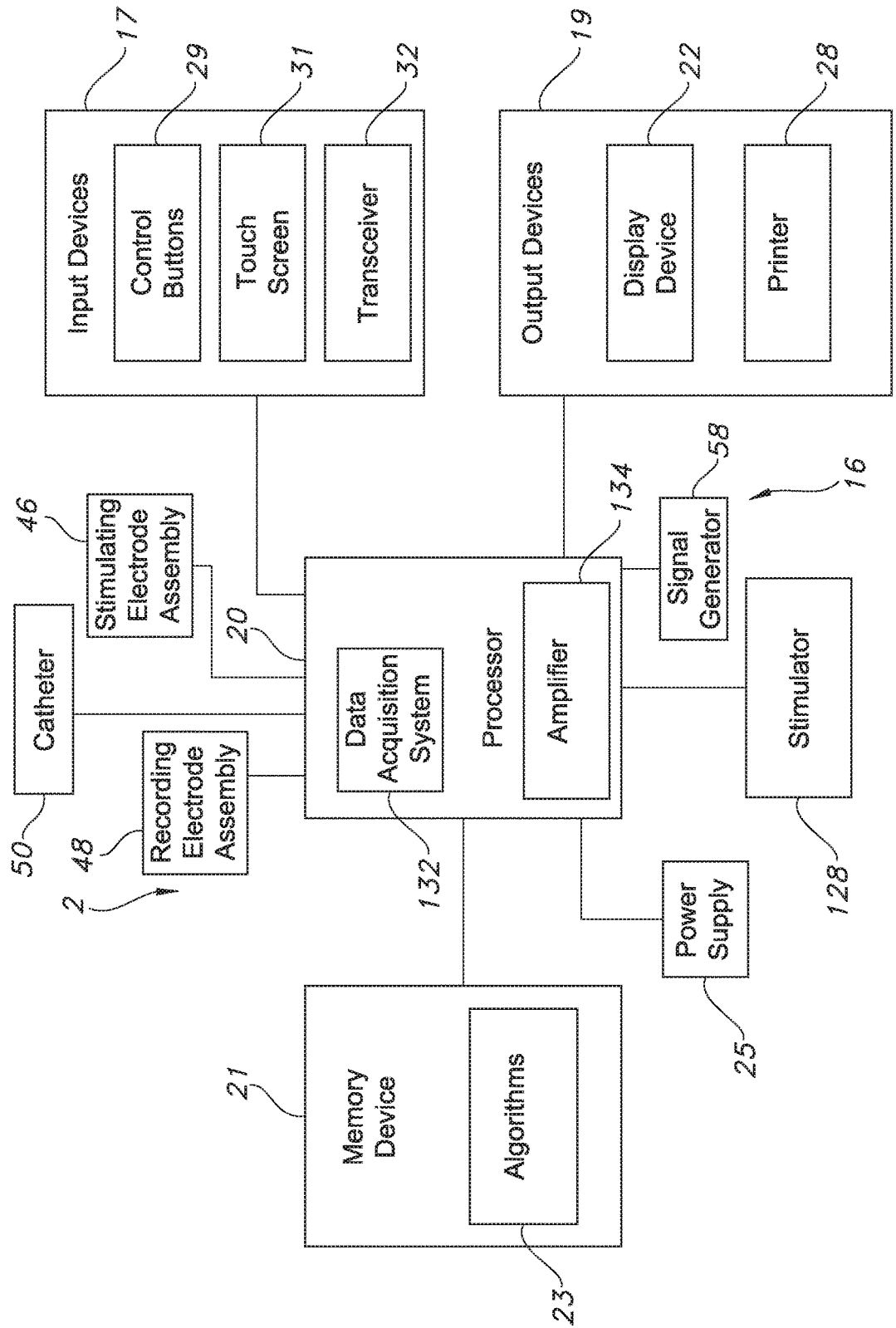
FIG. 2 is a schematic block diagram of the electronic configuration of the catheter position guidance system illustrating the processor, memory device, catheter, stimulation electrodes, recording electrodes, stimulator, input devices, output devices, and optional signal generating assembly according to one embodiment of the present invention.
Figure 3:
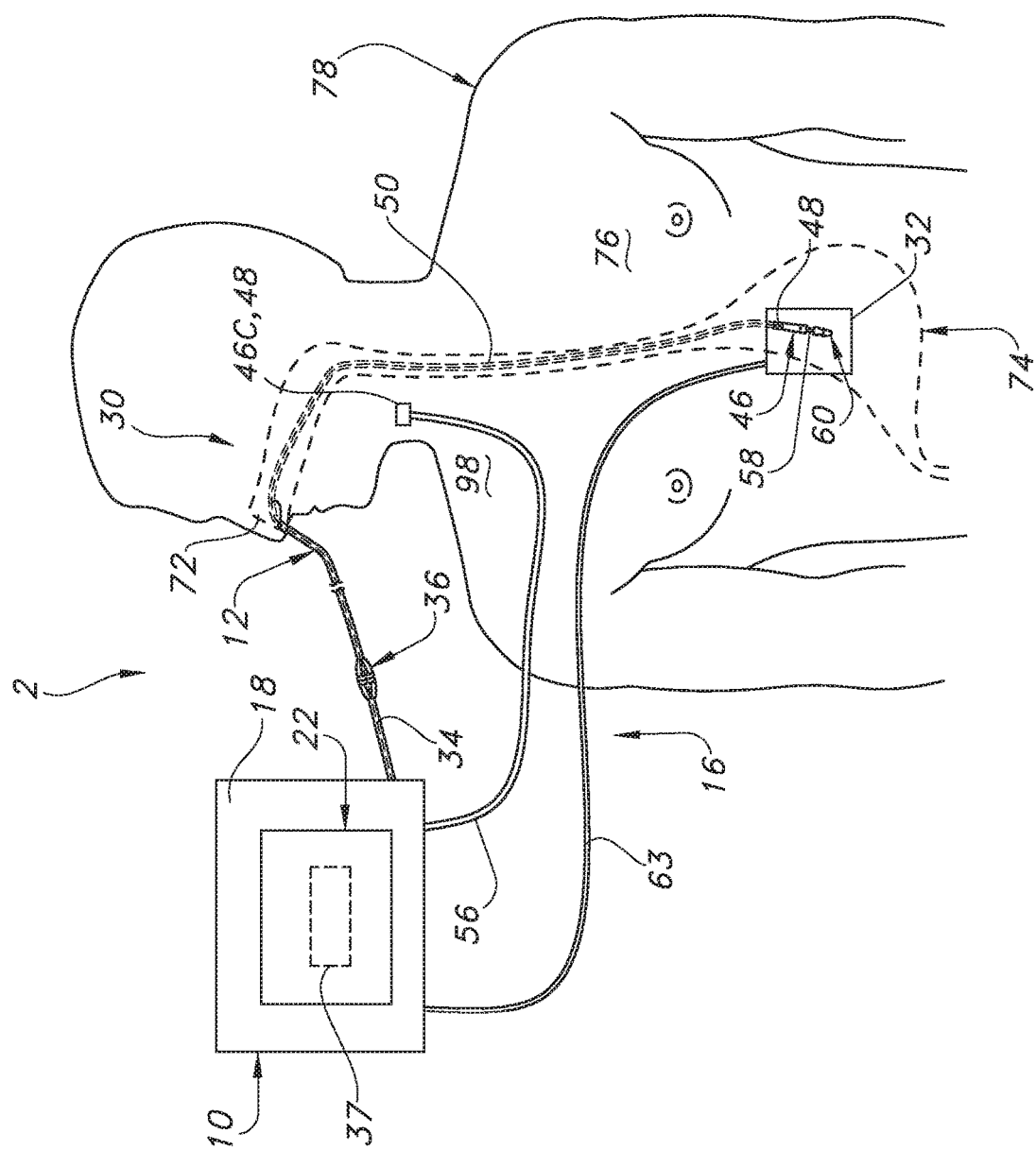
FIG. 3 is a top or plan view of the electronic catheter unit and the display device illustrating an enteral application involving inserting a catheter into a human body and indication of information recorded from the recording electrodes in response to a waveform delivered from the stimulator to the stimulation electrodes (e.g., a graph) on the display device.

As best illustrated in FIG. 2, the system 2, in one embodiment, includes: (a) a plurality of input devices 17 for providing input signals to the system 2 such as one or more control buttons 29, a touch screen 31, and the optional transceiver 32; (b) a stimulation electrode assembly 46; (c) a recording electrode assembly 48 that can continuously capture electrical activity elicited by tissue near the catheter 50 of the tubing assembly 14 in real-time; (d) a stimulator 128 which sends electrical signals in the form of a waveform via the stimulation electrode assembly 46; (e) an optional signal generator 58 which produces or generates electronic signals that are received by the transceiver 32; (f) a memory device 21 including machine readable instructions and one or more computer programs (which, for example, may include a plurality of algorithms 23) which are used by the processor 20 to process the electrical activity data captured by the recording electrode assembly 48 as well as to process the signal data produced by the signal generator 58 and transmitted by the transceiver 32 if present; (g) a data acquisition system 132; (h) a signal amplifier 134; and (i) a plurality of output devices 19 such as the display device 22 and the printer 28 which indicate the catheter information to the health care provider, such as in the form of a graph 37 (see FIG. 1). The display device 22 may be any suitable display mechanism including, but not limited to, a liquid crystal display (LCD), light-emitting diode (LED) display, cathode-ray tube display (CRT) or plasma screen.

In one particular embodiment, the memory device 21 can store instructions which, when executed by the processor 20, cause the processor 20 to (i) interpret catheter 50 location and/or position information as determined and communicated by the recording electrode assembly 48 based on the tissue's response to stimulation delivered from the stimulator 128 via the stimulation electrode assembly 46 and the optional signal generating assembly 16 (including the signal generator 58 and the non-invasive transceiver 32), and (ii) cause the processor 20 to then instruct the system 2 to alert the health care provider either via the display device 22, auditory signals, etc. as to the accurate or inaccurate placement of the catheter 50.

Figure 4:
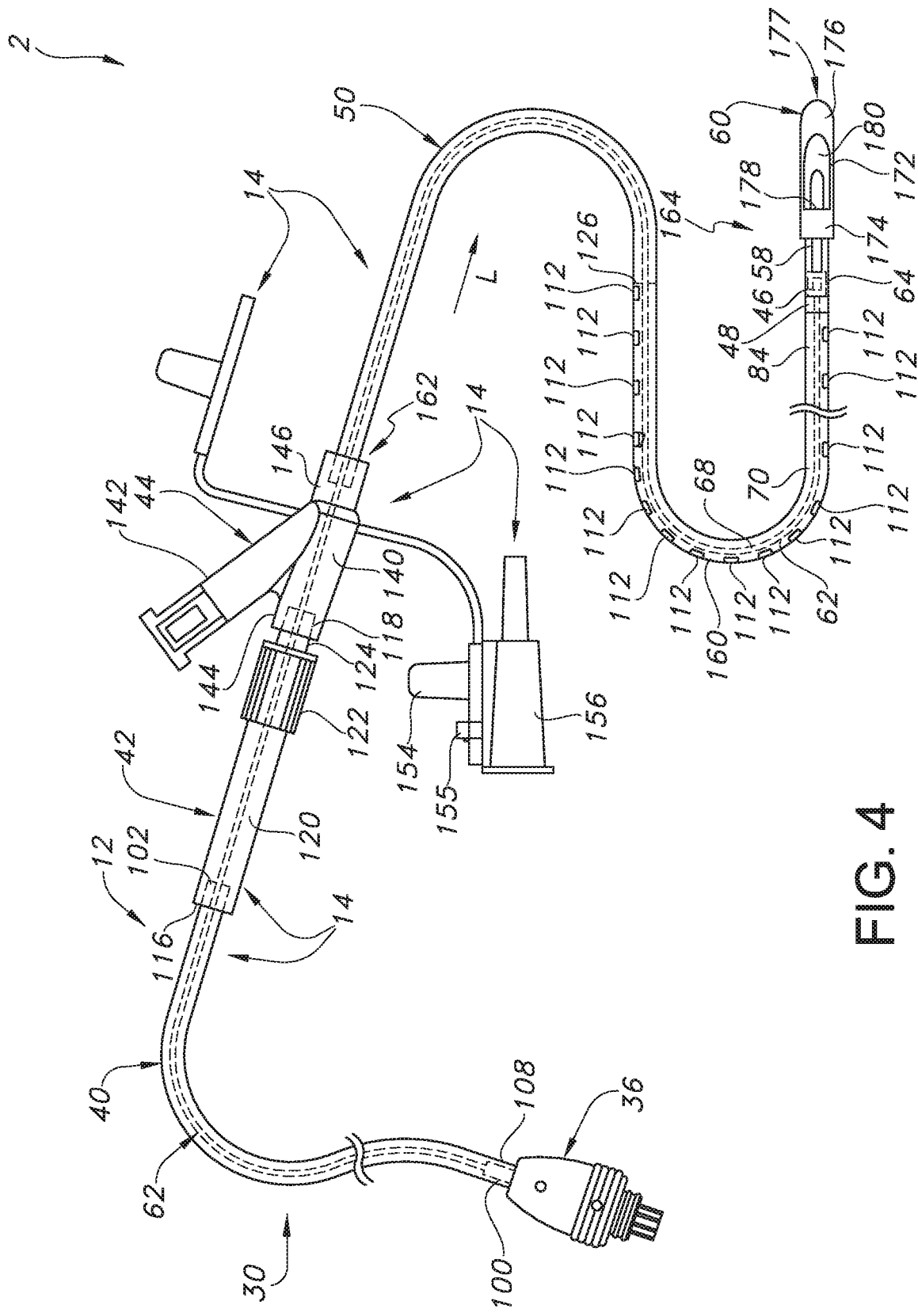
FIG. 4 is a perspective view of the electronic catheter unit illustrating the various components in more detail.

Health care providers can use the system 2 in a variety of catheter applications. In one example illustrated in FIG. 3, the system 2 is used in an enteral application. Here, a portion of the electronic catheter unit 12 is placed through an orifice 72 of the patient, such as the patient's nose or mouth. The distal end or tip 60 of the electronic catheter unit 12 can ultimately by positioned in the stomach 74. As the health care provider advances the catheter 50 of the electronic catheter unit 12 towards the patient's stomach 74, the stimulator 128 can be activated to deliver a stimulation waveform to the stimulation electrode assembly 46 while the recording electrode assembly 48 can continuously monitor for electrical activity elicited by tissue near the distal end 60 of the catheter 50 where at least one electrode in the stimulation electrode assembly 46 is positioned as the catheter 50 is inserted by the health care provider, as shown in FIGS. 1 and 4. The stimulation electrode assembly 46 and the recording electrode assembly 48 can each include a plurality of electrodes as will be discussed in more detail with respect to FIGS. 5 and 6, where it is to be understood that one or more of the electrodes in the recording electrode assembly 48 and/or a surface electrode 46c of the stimulation electrode assembly 46 can be present on a surface of skin 98 such that the stimulation and/or recording of electrical activity can be achieved transcutaneously. The display device 22 and/or the printer 28 can indicate information related to the location of the portion of the electronic catheter unit 12 within the body 78 based on the electrical activity data acquired by the recording electrode assembly 48, as well as information related to the shape of the pathway taken by the catheter unit 12 if the system includes a signal generating assembly 16 that utilizes the signal generator 58 and the associated non-invasive transceiver 32. It should be appreciated that the system 2 need not indicate the exact location or path of the catheter unit 12 to provide assistance to the health care provider.

Figure 5:
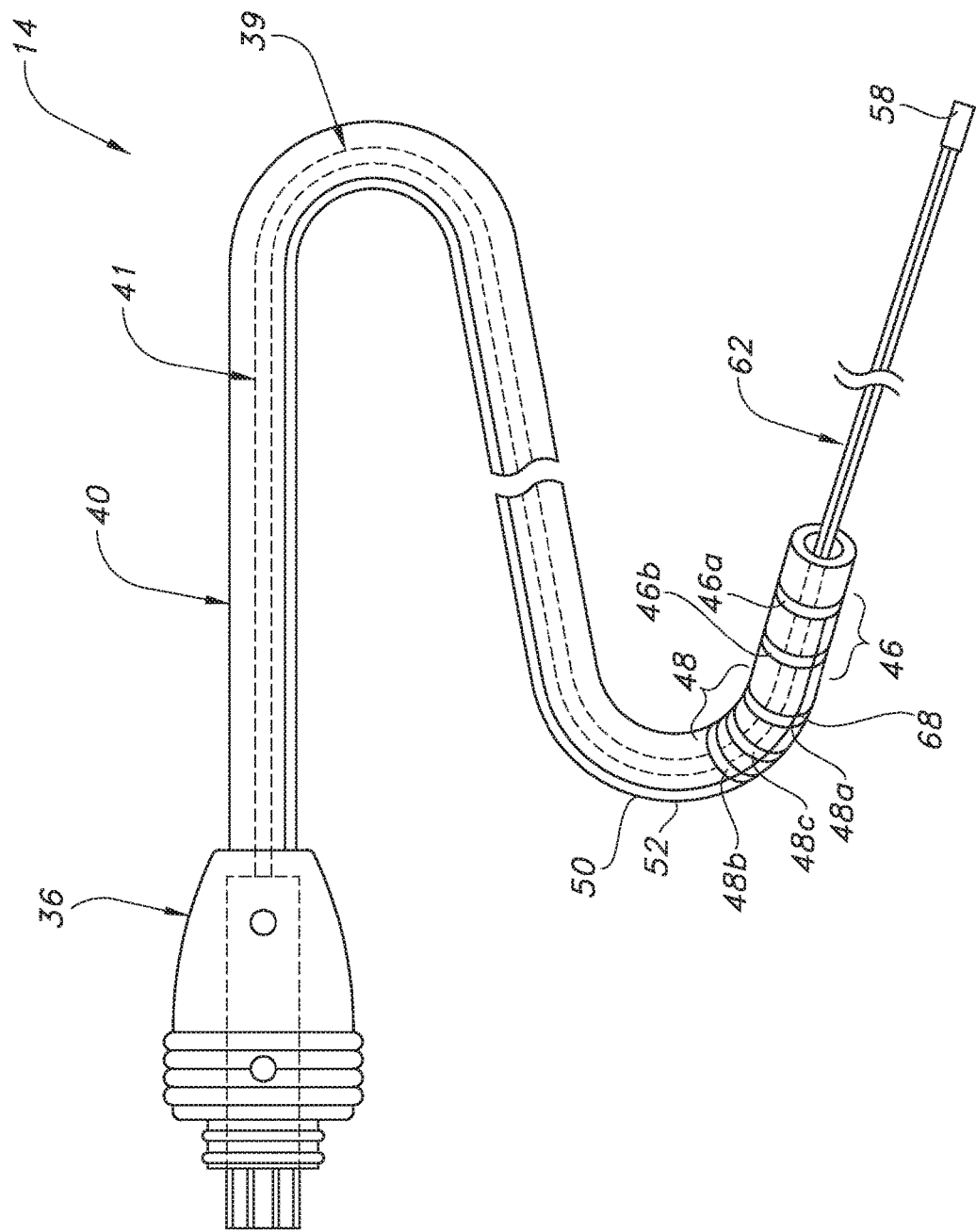
FIG. 5 is a perspective view of the electrode and optional signal generator portions of the electronic catheter unit according to one embodiment of the present invention.
Figure 6:
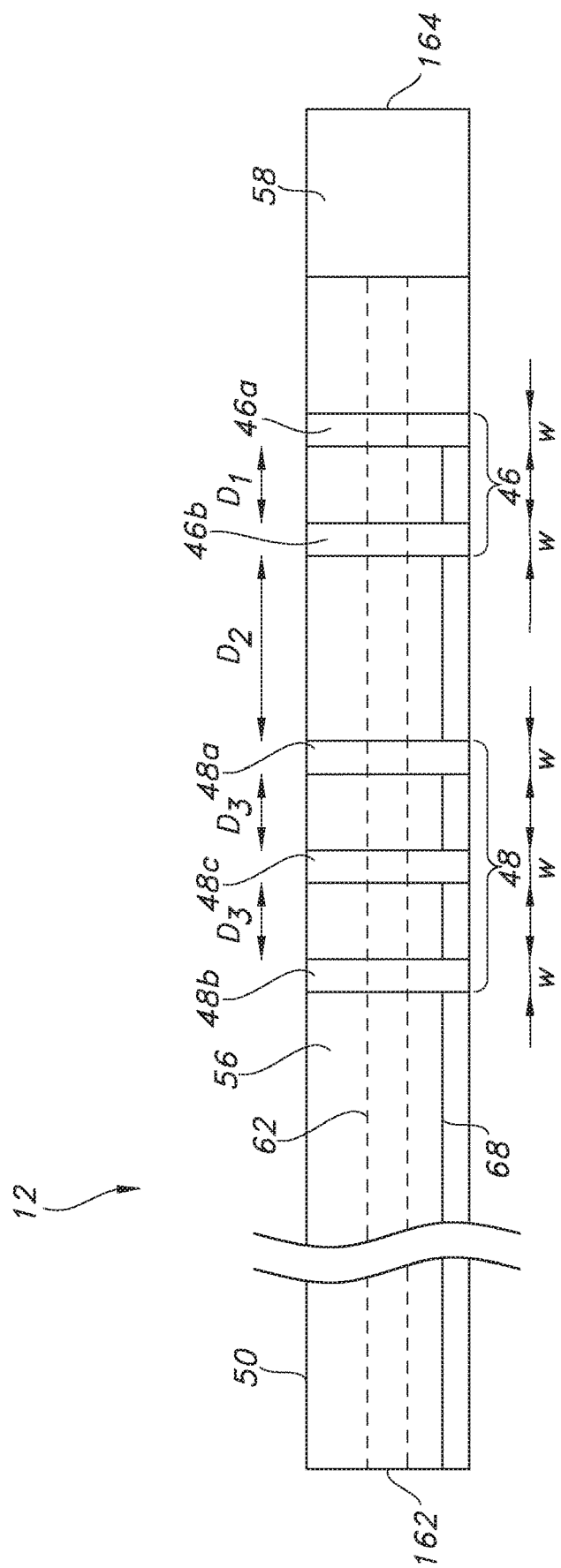
FIG. 6 is a side view of the electrode and optional signal generator portions of the electronic catheter unit according to one embodiment of the present invention.

Referring to FIGS. 4-6, in one embodiment, the electronic catheter unit 12 includes a tubing assembly 14, which includes the catheter 50, at least a portion of the stimulation electrode assembly 46, and optionally at least a portion of the recording electrode assembly 48. The catheter 50 includes a lumen 70 defined between a proximal end 162 and a distal end 164 to define a catheter body 160, where the catheter 50 can generally extend in the longitudinal direction L. Further, in one embodiment, at least a portion of the stimulation electrode assembly 46 and at least a portion of the recording electrode assembly 48 can be disposed on an outer wall 52 of the catheter, at a distal end 164 of the catheter 50 or tip 60 of the electronic catheter unit 12, as shown in FIG. 4. However, it is also to be understood that a portion of the stimulation electrode assembly 46 and all or a portion of the recording electrode assembly 48 can be positioned on a surface of skin 98 so long as the stimulation waveform delivered to an area of tissue by the stimulation electrode assembly 46 can reach the area of tissue at levels sufficient to elicit an electrical response and the electrical activity elicited by tissue in response to the stimulation waveform can be adequately recorded by the recording electrode assembly 48.

In one embodiment, for instance, a surface electrode 46c of the stimulation electrode assembly 46 and one or more electrodes of the recording electrode assembly 48 can be located on a surface of skin 98. The surface electrode 46c can be used when the electrical stimulation waveform is delivered by the stimulation electrode assembly 46 in monopolar fashion, while a cathode 46a and an anode 46b disposed on an outer wall 52 of the catheter 50 can be used in the electrical stimulation waveform delivered by the stimulation electrode assembly 46 is delivered in bipolar fashion. Further, the recording electrode assembly 48 can include an active recording electrode 48a, an inactive recording electrode 48b, and a reference electrode 46c, each of which can also be disposed on the outer wall 52 of the catheter anywhere along its length or can be disposed on a surface of skin 98. Further, as shown in FIGS. 1 and 5-6, when any of the electrodes or located on the outer wall 52 of the catheter 50, the electrodes (e.g., the stimulation electrode assembly 46 and/or recording electrode assembly 48) can be electrically connected to the apparatus 10 via an electrode electrical connection 68, which can be in the form of a wire or printed conduit. However, it is also to be understood that the connection can be wireless. Moreover, when any of the electrodes are located on a surface of skin 98 for transcutaneous stimulation and/or recording, the electrodes (e.g., the stimulation electrode assembly 46 and/ or recording electrode assembly 48) can be electrically connected to the apparatus 10 via a wire 56. However, it is also to be understood that the connection can be wireless.

Referring to FIGS. 5 and 6, the stimulation electrode assembly 46 can be disposed on the outer wall 52 of the catheter 50 at distal end 164 of the catheter 50, while the recording electrode assembly 48 can also be disposed at the distal end 164 or can be disposed anywhere along the length of the catheter 50 between the proximal end 162 and the distal end 164. In any event, the cathode 46a and the anode 46b of the stimulation electrode assembly 46 and the active recording electrode 48a, the inactive recording electrode 48b, and the reference electrode 48c of the recording electrode assembly 48 can each have a width W ranging from about 0.1 millimeters to about 10 millimeters, such as from about 0.25 millimeters to about 5 millimeters, such as from about 0.5 millimeters to about 2.5 millimeters and can encircle all or a portion of the catheter wall 52 in the form of a ring, a stent-like embodiment, an expandable balloon, etc. In addition, the cathode 46a and the anode 46b can be separated by a distance D1 ranging from about 1 millimeter to about 10 millimeters, such as from about 2 millimeters to about 8 millimeters, such as from about 4 millimeters to about 6 millimeters. Moreover, the stimulation electrode assembly 46 and the recording electrode assembly can be separated by a distance D2 ranging from about 2 millimeters to about 20 millimeters, such as from about 4 millimeters to about 16 millimeters, such as from about 8 millimeters to about 12 millimeters. Lastly, the active recording electrode 48a and the reference electrode 48c as well as the inactive recording electrode 48b and the reference electrode 48c, can be separated by a distance D3 ranging from about 1 millimeter to about 10 millimeters, such as from about 2 millimeters to about 8 millimeters, such as from about 4 millimeters to about 6 millimeters.

In addition, the components of the stimulation electrode assembly 46, the recording electrode assembly 48, and any other electrical components can be formed from MRI compatible materials such that the catheter guidance system 2 can be used in patients undergoing MRI or other diagnostic testing where magnetic components cannot be used. For instance, carbon or any other non-magnetic materials can be used.

As best illustrated in FIGS. 4-5, in one embodiment, such as when a wired connection (e.g., a connection via a physical electrode electrical connection 68 as opposed to a wireless connection, which is also contemplated by the present invention, where the stimulation electrode assembly 46 and/or the recording electrode assembly 48 include a battery or other source of power) electrically connects the stimulation electrode assembly 46 and the recording electrode assembly 48 to the processor 20, the tubing assembly 14 can also include (a) a tube or an electrical tubular insulator 40; (b) a mid-connector or union device 42 which receives the tubular insulator 40; (c) a multi-port connector or y-port connector 44 attachable to the union device 42; (d) a catheter 50, such as a feeding tube, connected to the y-port connector 44; and (e) a distal end or tip 60 of the catheter 50, where at least a portion of the stimulation electrode assembly 46 and optionally the recording electrode assembly 48 can be located on an outer wall 52 of the catheter 50 at the distal end or tip 60 or where the recording electrode assembly 48 can be located anywhere upstream along the length of the catheter 50. Components (a) through (c) can also be used to electrically connect the optional signal generator 58 via wire assembly 62 as discussed in more detail below.

In one embodiment, the tubular insulator 40 includes a tube having a proximal end 100 attachable to an attachment member or neck 108 of a controller coupler or electrical connector 36 and a distal end 102 receivable by the union device 42; and an internal diameter which is substantially equal to or greater than an external diameter of a wire assembly 62 and the electrode electrical connection 68, which can serve as the hard wired electrical connection between the portions of the stimulation electrode assembly 46 and the recording electrode assembly 48 present on the outer wall 52 of the catheter 50 signal generator 58 and the processor 20, so as to slide over the electrical electrode connection 68 and the wire assembly 62. In another embodiment, the tubular insulator 40 may fit relatively tightly over the electrical electrode connection 68 and the wire assembly 62.

As best illustrated in FIG. 4, in one embodiment, the union device 42 includes: (a) a proximal end 116; (b) a distal end 118; (c) a position adjuster, extender or elongated neck 120 positioned between the proximal end 116 and the distal end 118; (d) a grasp or gripping member 122 positioned adjacent to the distal end 118 so as to assist users in grasping and manipulating the union device 42; and (e) an insert 124 positioned adjacent to the gripping member 122 which is received by the y-port connector 44. When assembled, the proximal end 116 of the union device 42 is coupled to the distal end 102 of the tubular insulator 40.

In one embodiment, the multi-port or y-port connector 44 includes: (a) a body 140; (b) a liquid delivery branch, medicine delivery branch or medicine branch 142 attached to the body 140 for distributing drugs, medicine or other medicinal liquids to the patient; (c) a nutrient delivery branch or feeding branch 144 attached to the body 140 and sized to receive the insert 124 of the union device 42; (d) a catheter or feeding tube connection branch 146 attached to the catheter 50; (e) a flexible or movable arm 148 attached to the body 140; and (f) a flexible or movable arm 150 attached to the body 140. In an alternative embodiment, y-port connector 44 includes additional branches for administering various nutrients or medicines to the body 78. In another alternative embodiment, the y-port connector 44 includes only a feeding branch 144 and a connection branch 146. The arm 148 has a stopper 152, and the arm 150 has a stopper 154. The stoppers 152 and 154 are sized to prevent fluid from passing through the branches 142 and 144 after such branches 142 and 144 are plugged with stoppers 152 and 154, respectively. In addition, the arm 150 includes a fastener 155 which secures a tube-size adapter 156 to the arm 150. The tube-size adapter 156 enables fluid delivery tubes (not shown) having various diameters to connect to the feeding branch 144 of the y-port connector 44.

As illustrated in FIG. 4, in one embodiment, the catheter 50 includes a feeding tube or catheter 50 with a body 160 having a proximal end 162 attached to the catheter connection branch 146 of the y-port connector 44 and a distal end 164. The proximal end 162 is insertable into the catheter connection branch 146 of the y-port connector 44 so as to bring the catheter 50 into fluid communication with the y-port connector 44.

As also shown in FIG. 4, in one embodiment, the end member, bolus or tip 60 is attached to the distal end 164 of the catheter 50. The tip 60 includes a body 172 having a collar 174 and an end member 176. The body 172 defines a passage 178 and an opening 180. The opening 180 is positioned between the collar 174 and the end member 176. A portion 177 of the end member 176 can have a rounded shape. The shape of the passage 178 and opening 180 of the tip 60 is configured to facilitate the flow of fluid from the catheter 50 into the patient's body while decreasing the likelihood that the opening 180 will become clogged.

The tubular connector 40, union device 42, y-port connector 44, catheter 50, and tip 60 can be made from any suitable polymer or plastic material including, but not limited to, polyamide, polyethylene, polypropylene, polyurethane, silicone and polyacrylonitrile.

Turning now to the specifics of the connection of the stimulation electrode assembly 46, the recording electrode assembly 48 (in some embodiments), and the optional signal generator 58 to the system 2, and referring to FIGS. 1, 4, and 5, a controller coupler or an electrical connector 36 can be operatively connected to the electrical extension 34 and an electrode electrical connection 68 can be operatively coupled to the electrical connector 36 to form a wired connection between the electrode assemblies and the processor 20 and any other electrical components of the system 2. In addition, an elongated wire assembly 62 can be operatively coupled to the electrical connector 36 to form a wired connection between the signal generator 58 and the processor 20, although it is to be understood that all of the electrical connections can be wireless. Further, a wire or elongated stiffener 39 can be attached to the connector 36 and can serve as a support for the wire assembly 62 when it is inserted into the body 160 of the catheter 50. Additionally, the tubular insulator 40 described above can cover a portion 41 of the wire assembly 62 and the electrode electrical connection 48 positioned adjacent to the connector 36. In any event, the electrical connector or controller coupler 36 can provide the electrical connection between the apparatus 10 and the stimulation electrode assembly 46 as well as the recording electrode assembly 48 when the assemblies are hard wired to the catheter guidance system 2 via the electrode electrical connection 68.

Figure 7A:
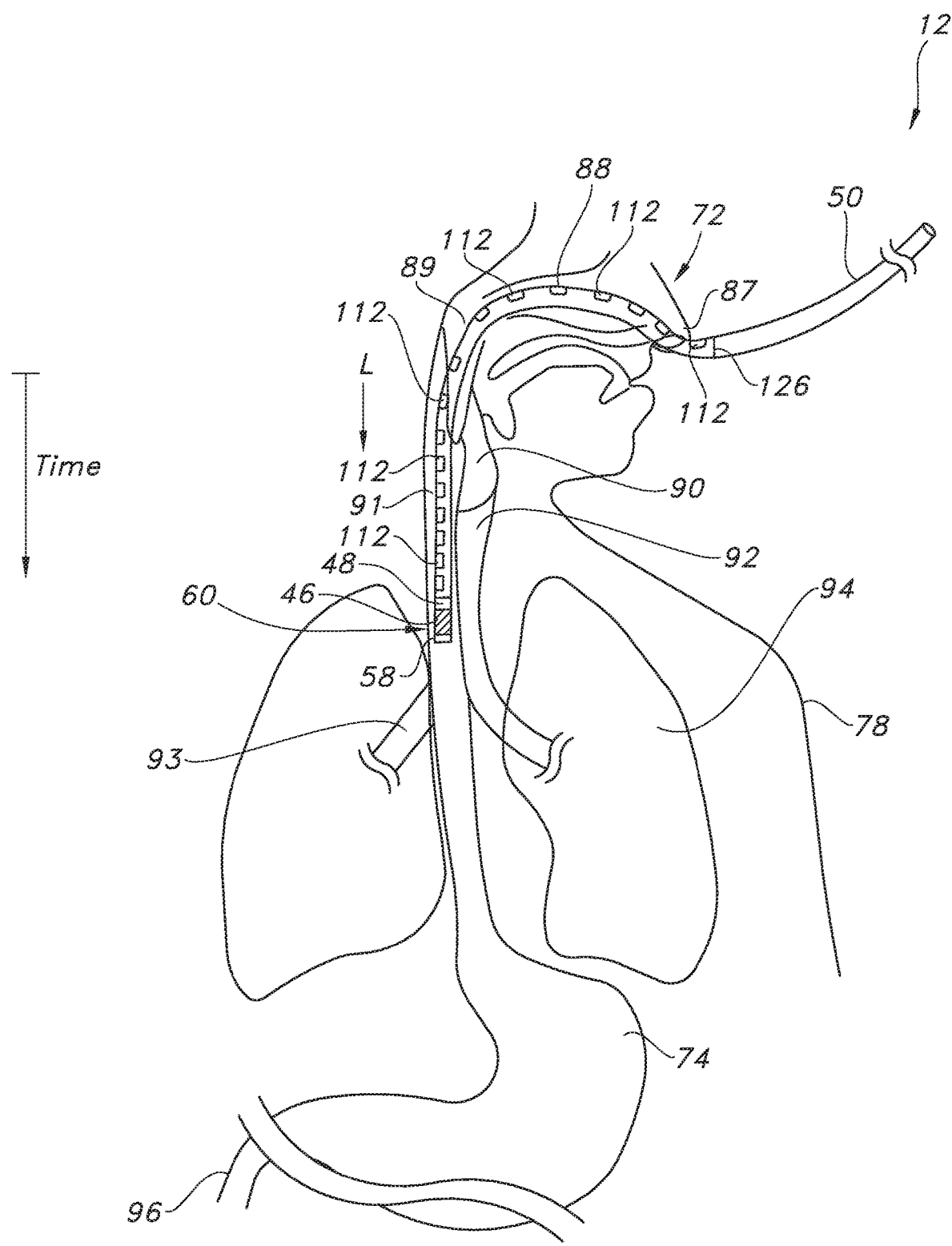
FIG. 7A is a top or plan view of a portion of the electronic catheter unit illustrating insertion of a catheter past the epiglottis of a patient and into the esophagus, where the anatomical location of the catheter within the body can be monitored via information recorded from the recording electrodes of the present invention in response to a waveform delivered from the stimulator to the stimulation electrodes of the present invention.
Figure 7B:
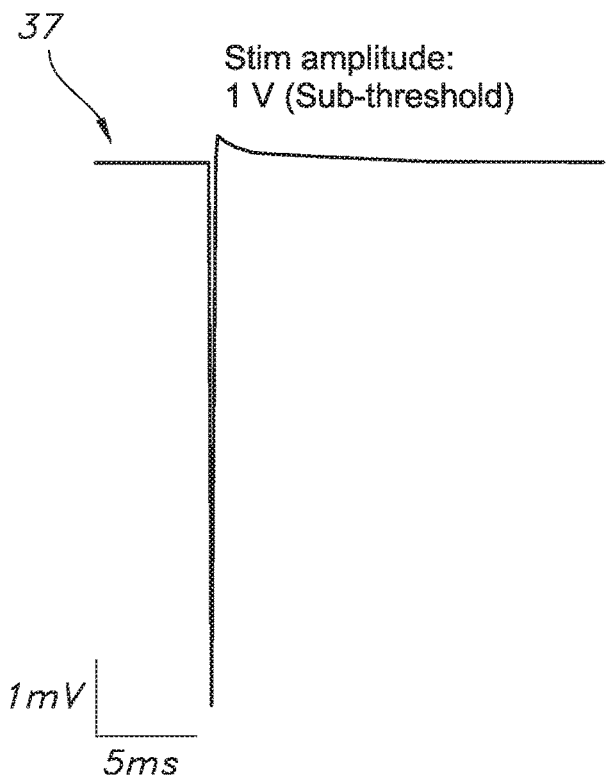
FIG. 7B is a graphical view of waveform data recorded by the recording electrodes of the catheter guidance system of the present invention as the catheter of FIG. 7A is inserted past the epiglottis in real-time when the stimulation waveform delivered from the stimulator to the stimulation electrodes is insufficient to elicit an evoked potential indicative of placement of the catheter in the esophagus.
Figure 7C:
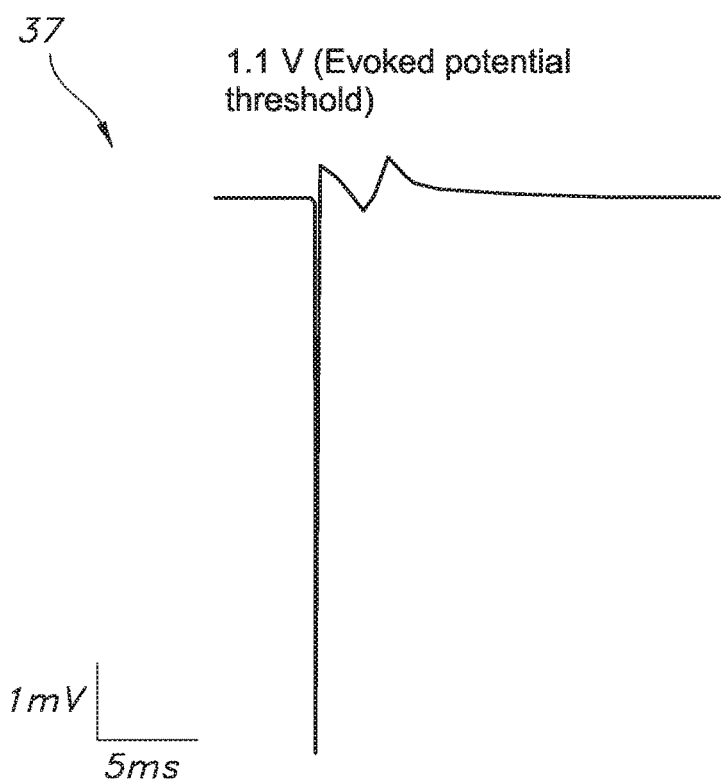
FIG. 7C is a graphical view of waveform data recorded by the recording electrodes of the catheter guidance system of the present invention as the catheter of FIG. 7A is inserted past the epiglottis in real-time when the stimulation waveform delivered from the stimulator to the stimulation electrodes is sufficient to elicit an evoked potential indicative of placement of the catheter in the esophagus.
Figure 7D:
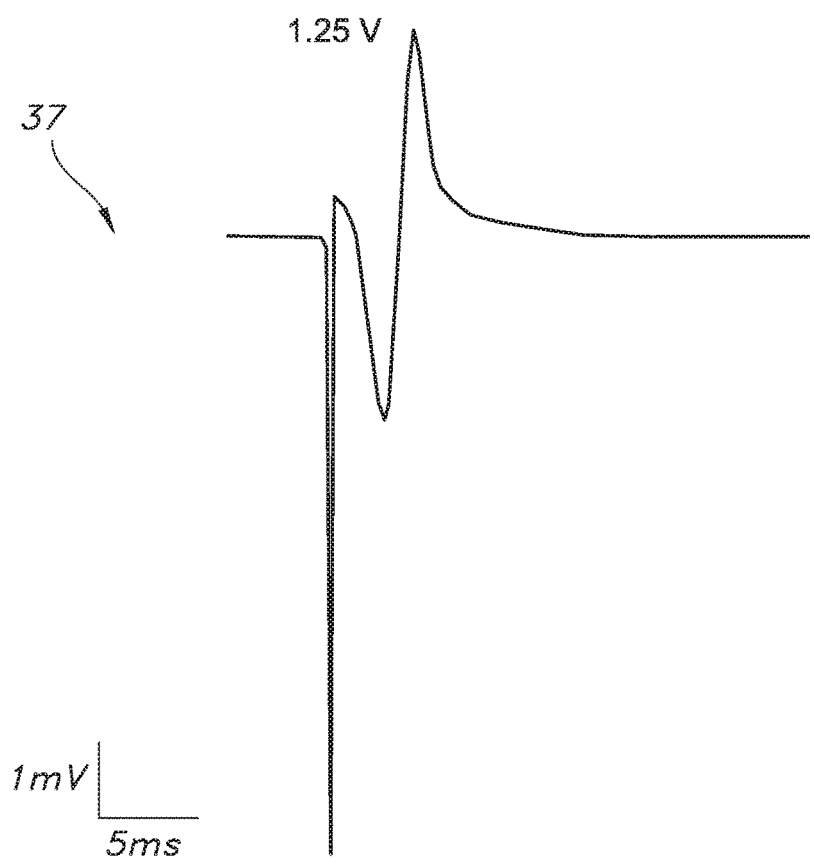
FIG. 7D is another graphical view of waveform data recorded by the recording electrodes of the catheter guidance system of the present invention as the catheter of FIG. 7A is inserted into the esophagus in real-time when the stimulation waveform delivered from the stimulator to the stimulation electrodes is sufficient to elicit an evoked potential indicative of placement of the catheter in the esophagus.
Figure 7E:
FIG. 7E is still another graphical view of waveform data recorded by the recording electrodes of the catheter guidance system of the present invention as the catheter of FIG. 7A is inserted past the epiglottis in real-time when the stimulation waveform delivered from the stimulator to the stimulation electrodes is sufficient to elicit an evoked potential indicative of placement of the catheter in the esophagus.
Figure 7F:
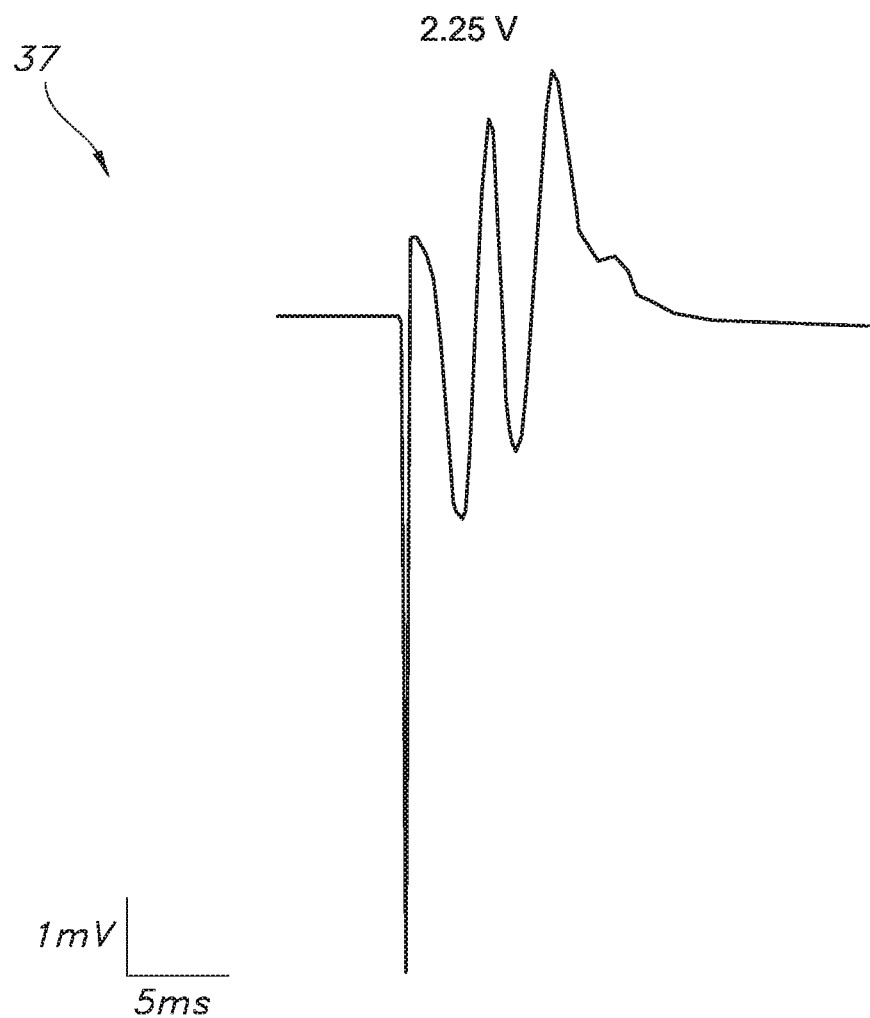
FIG. 7F is yet another graphical view of waveform data recorded by the recording electrodes of the catheter guidance system of the present invention as the catheter of FIG. 7A is inserted past the epiglottis in real-time when the stimulation waveform delivered from the stimulator to the stimulation electrodes is sufficient to elicit an evoked potential indicative of placement of the catheter in the esophagus.
Figure 7G:
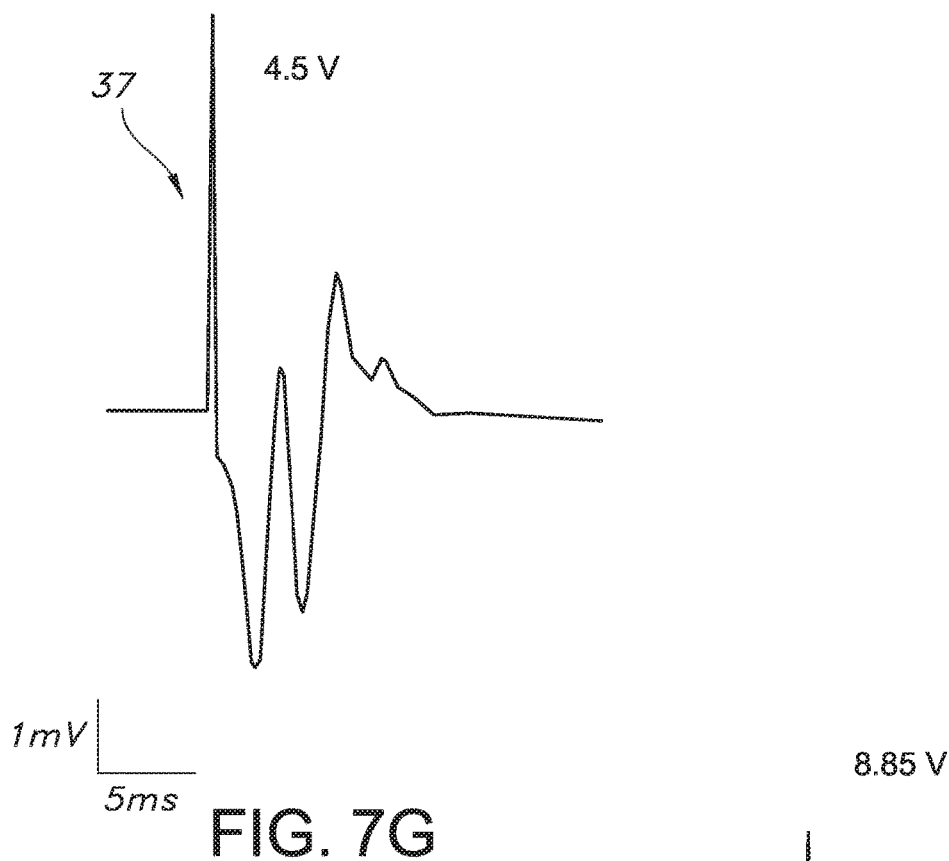
FIG. 7G is another graphical view of waveform data recorded by the recording electrodes of the catheter guidance system of the present invention as the catheter of FIG. 7A is inserted past the epiglottis in real-time when the stimulation waveform (reversed polarity) delivered from the stimulator to the stimulation electrodes is sufficient to elicit an evoked potential indicative of placement of the catheter in the esophagus.
Figure 7H:
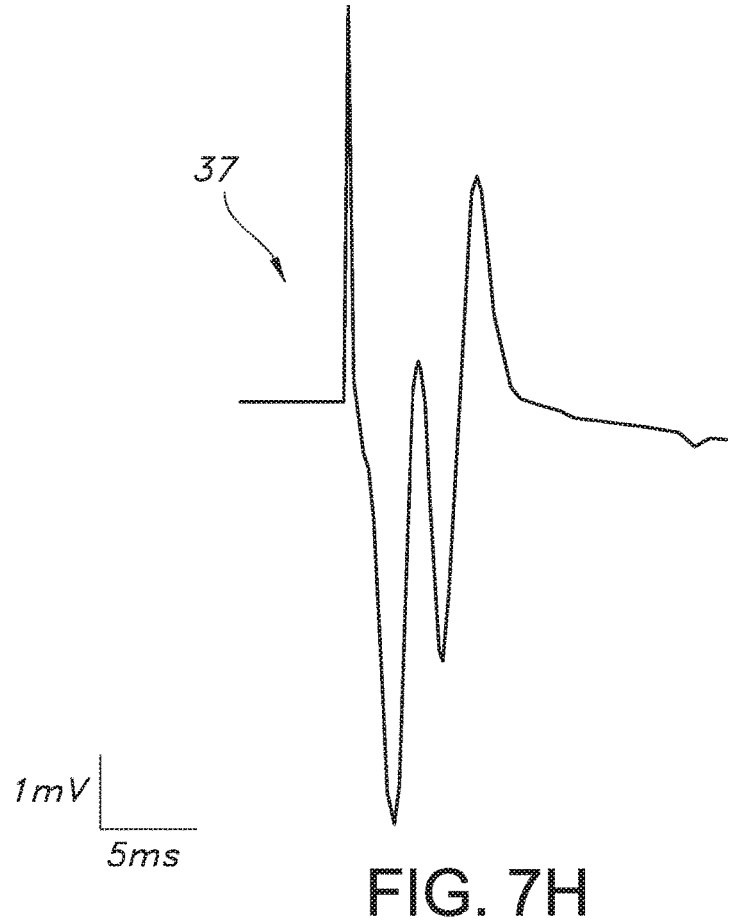
FIG. 7H is one more graphical view of waveform data recorded by the recording electrodes of the catheter guidance system of the present invention as the catheter of FIG. 7A is inserted past the epiglottis in real-time when the stimulation waveform (reversed polarity) delivered from the stimulator to the stimulation electrodes is sufficient to elicit an evoked potential indicative of placement of the catheter in the esophagus.

Further, in one embodiment and referring to FIGS. 4 and 7A, the catheter body 160 can have a plurality of markings 112 uniformly spaced along its external surface that can be used in conjunction with the stimulation electrode assembly 46 and the recording electrode assembly 48 to determine accurate placement of the catheter 50 and/or to determine the appropriate time during which to deliver the stimulation waveform from the stimulator 128 via the stimulation electrode assembly 46 and to initiate recording of the electrical activity elicited by tissue near the esophagus 91 of a patient via the recording electrode assembly 48. These markings 112 can function as placement markers which assist the user in assessing the depth that the catheter 50 is placed within the patient's body 78. For instance, when the stimulation electrode assembly 46 is located at the distal end 164 of the catheter 50, the markings 112 can be present from the distal end 60 of the electronic catheter unit 12 or the distal end 164 of the catheter 50 to a point 126 on the catheter 50 that spans a distance that can correspond with the average distance between the trachea 92 and nostril 87 in a typical patient. As the catheter 50 is being inserted into the body 78 via the nostril 87, once the markings 112 are no longer visible outside the body 78, the user can be alerted to start delivering an electrical stimulation waveform from the stimulator 128 via the stimulating electrode assembly 46 and to start monitoring the graphs 37 on the display device 22 to observe the data recorded by the recording electrode assembly 48 related to the electrical activity elicited by tissue in response to the stimulation or to start monitoring for a visual indication, auditory indication, or both that the catheter 50 has be inserted into the correct (e.g., digestive tract) or incorrect location (e.g., respiratory tract). For example, if the lack of an appearance of an evoked potential is shown on the display device 22 in response to the delivery of stimulation waveform to tissue near the distal end 164 or if an impedance versus time plot exhibits certain characteristics once the markings 112 are no longer visible outside the body 78, then the user will be able to determine that the catheter 50 has been improperly inserted into the trachea 92 instead of the esophagus 91, and the catheter 50 can be immediately retracted. In an alternative embodiment, these markings 112 can assist the user in measuring the flow or distribution of liquid to or from the patient.

Now that the specific components of the catheter guidance system 2 have been discussed in detail, a method of using the catheter guidance system 2 of the present invention in order to verify the accurate placement of a catheter 50 used for enteral feeding in the digestive tract is discussed in more detail below with reference to FIGS. 7A-9B.

Generally, the method for determining if the catheter 50 is accurately placed within a digestive tract (e.g., the esophagus of a body 78 of a patient includes inserting a distal end of the tubing assembly 14 (e.g., the distal end 164 of the catheter 50 or tip 60 of the electronic catheter unit 12) into an orifice 72 of the body 78, such as a nostril 87 of the patient's nose. As described above, the tubing assembly 14 can include the catheter 50, at least a portion of the stimulation electrode assembly 46 (part of which can be placed transcutaneously on a surface of skin 98), the recording electrode assembly 48 (or, alternatively all or a portion of the recording electrode assembly 48 can be placed transcutaneously on a surface of skin 98) and the optional signal generator 58. Once the tubing assembly 14 is inserted into the orifice 72 of the body 78, the stimulation electrode assembly 46, the recording electrode assembly 48, and the optional signal generator 58 can be electrically connected to a processor 20 via a wired connection, such as the electrode electrical connection 68 and the wire assembly 62, although a wireless connection is also contemplated by the present invention such that no electrode electrical connection 68, wire assembly, 62 or controller coupler 36 is required.

Next, the stimulation electrode assembly 46 is activated, such as by providing power to stimulator 128 connected to the stimulation electrode assembly 46, and the stimulation electrode assembly 46 then begins to deliver a stimulation waveform to tissue near the distal end 164 of the catheter/the tip or distal end 60 of the electronic catheter unit 12 via the stimulation electrode assembly 46. At the same time, the recording electrode assembly 48 can be activated to begin to record the electrical activity (e.g., muscle activity or twitches in the form of action potentials, impedance measurements, etc.) elicited by the tissue in response to the stimulation waveform. The recording electrode assembly 48 then communicates with the processor 20 via the wired connection (e.g., connection 68) or the wireless connection to deliver the acquired electrical activity data to the processor 20 in real-time.

The stimulation waveform can have various features depending on the electrical activity to be monitored. For instance, when monitoring for electrical muscle activity in response to stimulation, where the muscle activity is in the form of evoked potentials, indicating activation of muscle tissue associated with the presence of the distal end 60 of the electronic catheter unit 12 in the esophagus 91, which contains striated muscle, or where there is insufficient activation of muscle tissue, indicating that the distal end 60 of the electronic catheter unit 12 has been inserted into the trachea, which contains cartilage such that no evoked potential is present, the stimulation waveform can be a constant-current or constant voltage square waveform (monophasic or biphasic). For instance, the stimulation waveform can have a stimulation amplitude ranging from greater than 1 volt to less than 150 volts, such as from about 1.01 volts to about 100 volts, such as from about 1.05 volts to about 50 volts, such as from 1.1 volts to about 25 volts. Alternatively, the stimulation waveform can have a stimulation waveform of less than 50 milliamps, such as from about 0.5 milliamps to about 50 milliamps, such as from about 1 milliamp to about 25 milliamps, such as from about 1.5 milliamps to about 10 milliamps. Further, the stimulation waveform can have a frequency ranging from about 0.01 hertz to about 100 hertz, such as from about 0.1 hertz to about 75 hertz, such as from about 0.5 hertz to about 50 hertz. In addition, the stimulation waveform can have a pulse width of less than 25 milliseconds, such as from about 0.5 milliseconds to about 20 milliseconds, such as from about 1 millisecond to about 15 milliseconds, such as from about 5 milliseconds to about 10 milliseconds.

On the other hand, when monitoring for changes in impedance in tissue based on the presence of the catheter 50 in the esophagus 91 or trachea 92, the stimulation waveform can be in the form of a noise signal having a frequency ranging from greater than 0 hertz to about 500 kilohertz, such as from about 1 kilohertz to about 300 kilohertz, such as from about 5 kilohertz to about 150 kilohertz, such as from about 10 kilohertz to about 125 kilohertz, and with the same stimulation amplitudes as described above. Because the impedance of esophageal tissue and tissue in the trachea have distinct characteristics, it can then be determined if the distal end 164 of the catheter 50/the distal end or tip 60 of the electronic catheter unit 12 is positioned in the esophagus or trachea.

In addition, a display device 22 can be coupled to the processor 20 and displays the electrical activity data communicated to the processor 20 by the recording electrode assembly 48 for a health care provider to use during the catheter insertion procedure, where the data may first pass through an amplifier 134 to amplify the frequencies of interest and through a data acquisition system 132 to digitize the recorded signals. The data can then be presented on the display device 22, where differences in the responses recorded by the recording electrode assembly 48 in response to the stimulation waveforms delivered by the stimulation electrode assembly 46 associated with catheter insertion into the digestive tract and into the respiratory tract can be easily identified by the health care provider via the graphs 37 on the display device 22. Alternatively or additionally, the memory device 21 can store instructions which, when executed by the processor 20, cause the processor 20 to interpret catheter 50 location and/or position information as determined and communicated by the optional signal generating assembly 16 and the non-invasive transceiver 32 and cause the processor 20 to then instruct the system 2 to alert the health care provider either via the display device 22, auditory signals, etc. as to the accurate or inaccurate placement of the catheter 50.

Specifically, when the electrical stimulation is in the form of a square-wave pulsed waveform, the appearance of evoked potentials on an amplitude versus time graph 37 that can be shown on the display device 22 can indicate placement of the catheter 50 in the digestive tract, where the evoked potentials are associated with activation of the muscle in the esophagus 91 near the distal end 60 of the electronic catheter unit 12. Meanwhile, the lack of appearance of such evoked potentials upon delivery of the square-wave pulsed waveform on an amplitude versus time graph 37 shown on the display device 22 can indicate erroneous placement of the catheter in the respiratory system (e.g., the trachea 92, bronchi 93, lungs 94, etc., or other anatomical region of the respiratory tract of the patient) at which time the insertion procedure should be stopped immediately and the tubing assembly 14 be removed from the respiratory tract to avoid potential harm to the patient. Further, in order for such information to be displayed or otherwise communicated by the display device 22, a memory device 21 stores instructions which, when executed by the processor 20, cause the processor 20 to (i) interpret the data communicated by the recording electrode assembly 48 and (ii) cause the display device 22 to communicate whether or not the catheter 50 is accurately placed within the digestive tract of the patient based on the interpretation of the electrical activity data.

Alternatively, when the electrical stimulation is in the form of a noise signal, a single frequency waveform, or multiple frequencies and one or more of the electrical contacts forming the stimulation electrode assembly or the recording electrode assembly 48 are utilized to measure the impedance of the tissue being contacted, the impedance measurements shown on an impedance versus time graph 37 on the display device 22 can indicate accurate placement of the catheter 50 in the digestive tract (e.g., the esophagus 91) or erroneous placement in the respiratory system (e.g., the trachea 92, bronchi 93, lungs 94, etc., or other anatomical region of the respiratory tract of the patient) at which time the insertion procedure should be stopped immediately and the tubing assembly 14 be removed from the respiratory tract to avoid potential harm to the patient. Further, in order for such information to be displayed or otherwise communicated by the display device 22, a memory device 21 stores instructions which, when executed by the processor 20, cause the processor 20 to (i) interpret the data communicated by the recording electrode assembly 48 and (ii) cause the display device 22 to communicate whether or not the catheter 50 is accurately placed within the digestive tract of the patient based on the interpretation of the electrical activity data.

The present inventors have found that the distinctions between the electrical activity elicited by tissue (e.g., electrical activity elicited by muscle in the esophagus versus electrical activity elicited by cartilage and/or muscle in the trachea) propagating from the opening 180 at the distal end 60 of the electronic catheter unit 12 and catheter 50 when the distal end or tip 60 of the electronic catheter unit 12 or catheter 50 is placed within the digestive tract or respiratory system are allow for an efficient and possibly life-saving determination of accurate enteral feeding catheter 50 placement in the digestive tract, where erroneously placing the catheter in the respiratory system would deliver fluid into the lungs, which can have fatal consequences.

For instance, as shown in FIGS. 7A through 7H, when the distal end or tip 60 of the electronic catheter unit 12 and catheter 50 is inserted into the nostril 87 of the patient and is advanced through the nasal cavity 88, past the nasopharynx 89, and into the esophagus 91 just past the epiglottis 90, as the recording electrode assembly 48 is continuously receiving, recording, and/or processing electrical activity elicited by tissue near the distal end 60 of the electronic catheter unit 12 and catheter 50 where the stimulation electrode assembly 46 is positioned or disposed, the amplitude versus time spectrogram graph 37 (FIG. 7B-71) displayed or otherwise communicated by the processor 20, such as via the display device 22, may show the presence of evoked potentials as the distal end or tip 60 of the electronic catheter unit 12 or catheter 50 travels into the digestive tract and not into the respiratory system, so long as the stimulation waveform amplitude is above a certain threshold. For instance, the stimulation amplitude of 1 volt in FIG. 7B was insufficient to elicit an evoked potential by the muscle in the esophagus 91 in response to the stimulation waveform, although the stimulation amplitudes of 1.1 volts (FIG. 7C), 1.25 volts (FIG. 7D), 1.5 volts (FIG. 7E), 2.25 volts (FIG. 7F), 4.5 volts, reversed polarity (FIG. 7G), and 8.85 volts, reversed polarity (FIG. 7H) were sufficient to elicit evoked potentials from the muscle in the esophagus.

Figure 8A:
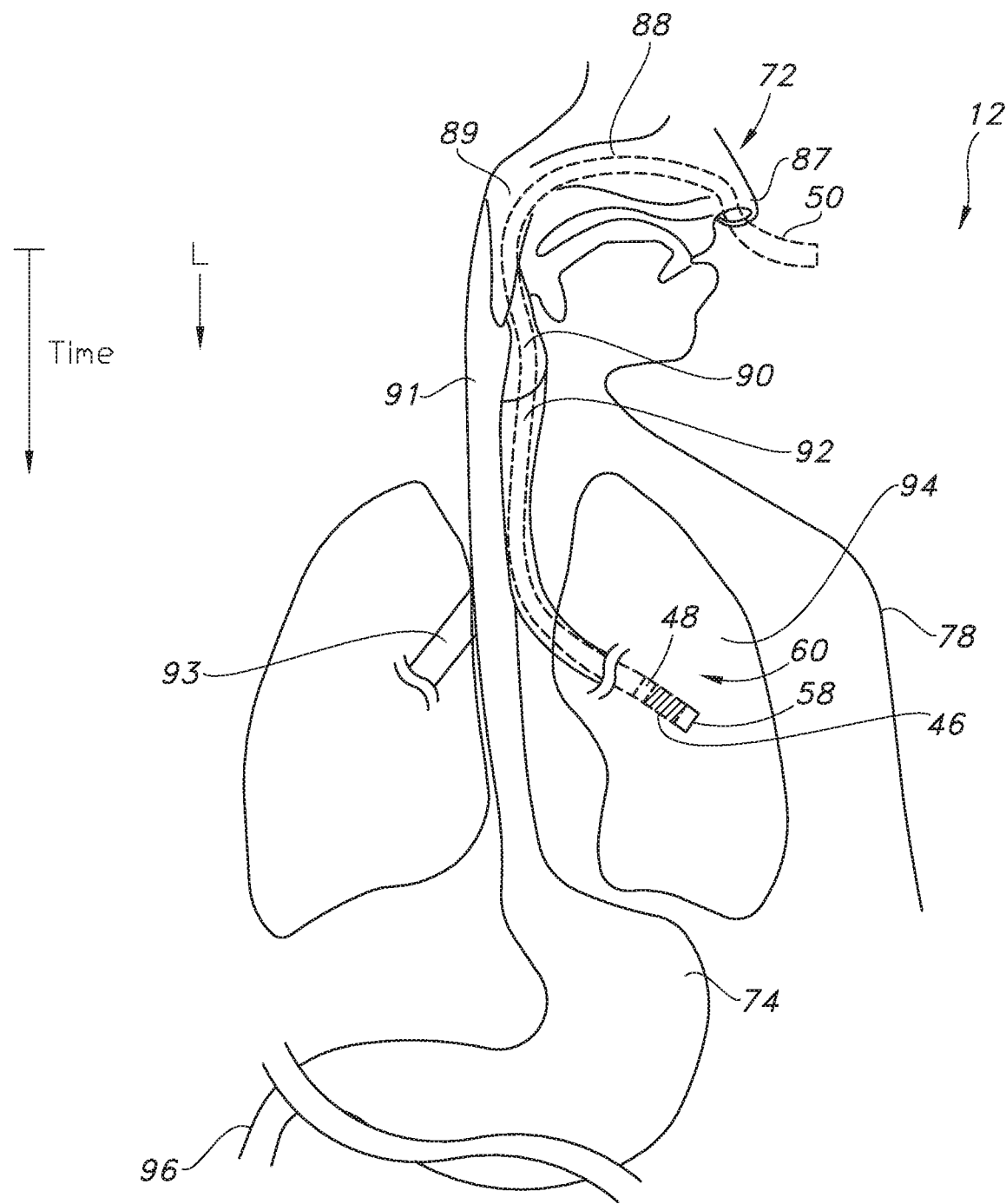
FIG. 8A is a top or plan view of a portion of the electronic catheter unit illustrating insertion of a catheter past the epiglottis and into the lung of a patient, where the anatomical location of the catheter within the body can be monitored via information recorded from the recording electrodes of the present invention in response to a waveform delivered from the stimulator to the stimulation electrodes of the present invention.
Figure 8B:
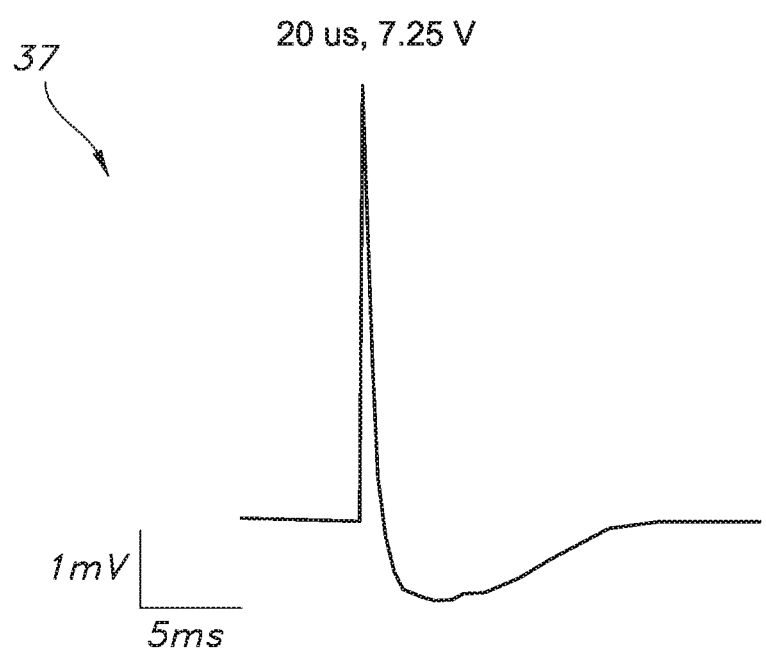
FIG. 8B is a graphical view of waveform data recorded by the recording electrodes of the catheter guidance system of the present invention as the catheter of FIG. 8A is inserted past the epiglottis in real-time when the stimulation waveform delivered from the stimulator to the stimulation electrodes would be sufficient to elicit an evoked potential indicative of placement of the catheter in the esophagus, where the lack of an evoked potential is indicative of placement of the catheter in the trachea.

On the other hand, as shown in FIGS. 8A and 8B, when the distal end or tip 60 of the catheter 50 is inserted into the nostril 87 of the patient and is advanced through the nasal cavity 88, past the nasopharynx 89, and into the trachea 92 just past the epiglottis 90, and then into the bronchi 93 or lungs 94, as the recording electrode assembly 48 is continuously receiving, recording, and/or processing electrical activity elicited by tissue near the distal end 60 of the electronic catheter unit 12 and catheter 50 where the stimulation electrode assembly 46 is positioned or disposed, the amplitude versus time spectrogram graph 37 (FIG. 8B) displayed or otherwise communicated by the processor 20, such as via the display device 22, may show the absence of evoked potentials as the distal end or tip 60 of the electronic catheter unit 12 or catheter 50 travels into the digestive tract and not into the respiratory system, so long as the stimulation waveform amplitude is above a certain threshold. For instance, the stimulation amplitude of 7.25 volts in FIG. 8B was insufficient to elicit an evoked potential in response to the stimulation waveform, although the stimulation amplitudes of 1.1 volts (FIG. 7C), 1.25 volts (FIG. 7D), 1.5 volts (FIG. 7E), 2.25 volts (FIG. 7F), 4.5 volts, reversed polarity (FIG. 7G), and 8.85 volts, reversed polarity (FIG. 7H) were sufficient to elicit evoked potentials from the muscle in the esophagus. This indicates that the catheter 50 in FIG. 8A is not placed in the esophagus 91 and is instead being inserted into the trachea 92. At this point, the health care provider can be alerted to remove the tubing assembly 14 from the respiratory system and start a new procedure to accurately place the distal end or tip 60 of the electronic catheter unit 12 or catheter 50 into the digestive tract for enteral feeding.

The present inventors have also found that the distinctions between the impedance measurements of tissue collected by the various electrical electrodes on the catheter (e.g., impedance data collected from electrodes placed in the esophagus versus impedance data collected from electrodes placed in the trachea) allow for an efficient and possibly life-saving determination of accurate enteral feeding catheter 50 placement in the digestive tract, where erroneously placing the catheter in the respiratory system would deliver fluid into the lungs, which can have fatal consequences.

Figure 9A:
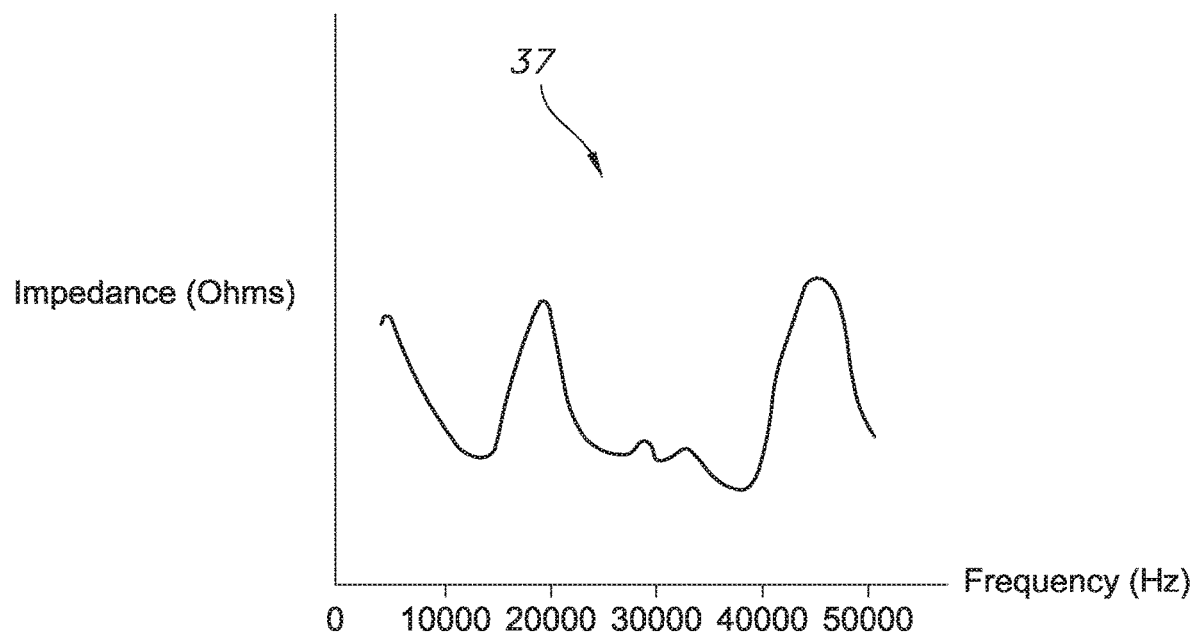
FIG. 9A is a graphical view of the impedance measured at an electrical contact at various frequencies as the catheter of FIG. 7A is inserted past the epiglottis in real-time, where the characteristics of the impedance values measured are in response to a noise signal that is delivered from the stimulator to the catheter and are indicative of placement of the catheter in the esophagus.

Specifically, FIG. 9A is a graphical view of the impedance of tissue measured at an electrical contact (e.g., any of the electrodes that are part of the stimulation electrode assembly 46 or the recording electrode assembly 48) when placed on the electronic catheter unit 12 or the catheter 50 at various frequencies as the electronic catheter unit 12 and catheter 50 of FIG. 7A is inserted past the epiglottis in real-time, where the characteristics of the impedance values measured are in response to a noise signal that is generated by the stimulator and delivered through the contacts onto the catheter and are indicative of the placement of the catheter within the esophagus. As shown, the impedance values (in Ohms) over a range of frequencies ranging from greater than 0 hertz to about 50,000 hertz show an impedance signature indicative of various peaks and valleys characteristic of esophageal tissue. Although FIG. 9A shows the impedance values measured when a noise signal is delivered to the tissue, it is also to be understood that that impedance can be measured at a single frequency (e.g., 5 kilohertz, 10 kilohertz, 25 kilohertz, 50 kilohertz, etc.), or can be measured when multiple frequencies are superimposed and delivered as one waveform (e.g., multiple sine waves delivered from the stimulator 128).

Figure 9B:
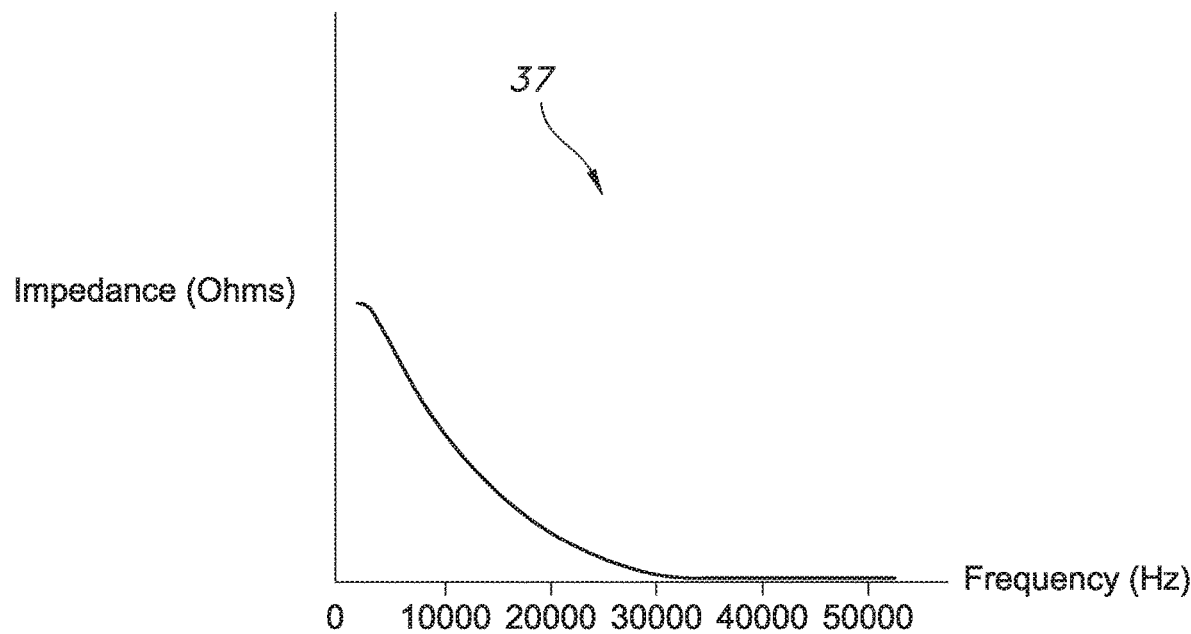
FIG. 9B is a graphical view of the impedance measured at an electrical contact at various frequencies as the catheter of FIG. 8A is inserted past the epiglottis in real-time, where the characteristics of the impedance values measured are in response to a noise signal that is delivered from the stimulator to the to the catheter and are indicative of erroneous placement of the catheter in the trachea.

Meanwhile, FIG. 9B is a graphical view of the impedance measured at an electrical contact (e.g., any of the electrodes that are part of the stimulation electrode assembly 46 or the recording electrode assembly 48) when placed on the electronic catheter unit 12 or the catheter 50 at various frequencies as the electronic catheter unit 12 and catheter 50 of FIG. 8A is inserted past the epiglottis in real-time, where the characteristics of the impedance values measured are in response to a noise signal that is generated by the stimulator and delivered through the contacts onto the catheter and are indicative of erroneous placement of the catheter in the trachea. As shown, the impedance values (in Ohms) over a range of frequencies ranging from greater than 0 hertz to about 50,000 hertz show an impedance signature indicative of tracheal tissue (e.g. exponentially decaying impedance values with increasing frequencies). Although FIG. 9B shows the impedance values measured when a noise signal is delivered to the tissue, it is also to be understood that that impedance can be measured at a single frequency (e.g., 5 kilohertz, 10 kilohertz, 25 kilohertz, 50 kilohertz, etc.), or can be measured when multiple frequencies are superimposed and delivered as one waveform (e.g., multiple sine waves delivered from the stimulator 128).

For instance, in one particular embodiment, utilizing a waveform having a stimulation frequency of 1000 hertz, the impedance values at various electrical contacts (e.g., any of the electrodes in the stimulation electrode assembly 46 or recording electrode assembly 48) made with tissue (e.g., esophageal tissue or tracheal tissue) can vary depending on the location of the catheter 50. When the catheter 50 is inserted in the esophagus and the impedance value is determined between the cathode 46*a* and the anode 46*b* of the stimulation electrode assembly 46, for instance, the impedance can be between 500 ohms and 600 ohms. Further, when the impedance value is determined between the active recording electrode 48*a* and the reference electrode 48*c* of the recording electrode assembly 48, the impedance can be between 900 ohms and 1000 ohms. Further, when the impedance value is determined between the inactive recording electrode 48*b* and the reference electrode 48*c*, the impedance can be between 950 ohms and 1050 ohms. In addition, when the impedance value is determined between the active recording electrode 48*a* and the inactive recording electrode 48*b*, the impedance can be between about 1000 ohms and 1100 ohms. Thus, regardless of the particular electrical contacts used when determining the impedance of tissue in the esophagus (e.g., epithelium, muscle, etc.), the impedance of the esophageal tissue is generally consistent.

On the other hand, when the catheter 50 is inserted in the trachea and the impedance value is determined between either between the cathode 46*a* and the anode 46*b* of the stimulation electrode assembly 46, between the active recording electrode 48*a* and the reference electrode 48*c* of the recording electrode assembly 48, between the inactive recording electrode 48*b* and the reference electrode 48*c*, or between the active recording electrode 48*a* and the inactive recording electrode 48*b*, the impedance is around 2000 ohms and is intermittent. This illustrates that the impedance signature collected from electrodes placed in the esophagus is distinct from the impedance signature collected from electrodes placed in the trachea, such that impedance measurements in response to a stimulation waveform can be utilized to determine the proper placement of a catheter in the respiratory tract. Without intending to be limited by any particular theory, the present inventors have found that the impedance signature of tissue in the trachea is minimal or exponentially decaying due to lack of contact with excitable tissue since the trachea is rigid due to the presence of cartilaginous tissue. Meanwhile, the impedance of esophageal tissue is generally consistent and has increased values due to the excitability of tissue in the esophagus (e.g., muscle capable of contracting).

Generally, the ratio of the impedance collected in the trachea to the impedance collected in the esophagus can be at least about 1.1:1, such as from about 1.25:1 to about 5:1, such as from about 1.5:1 to 4:1, such as from about 1.75:1 to about 3:1.

Moreover, as an alternative or in addition to recording the electrical activity elicited in response to the delivery of stimulation waveform, the health care provider can also verify accurate placement of the catheter 50 in the esophagus 91 rather than the trachea 92 by observing for the presence or absence of a plurality of markings 112 uniformly spaced along the external surface of the catheter 50. As described above, such markings 112 can be used in conjunction with the stimulation electrode assembly 46 and the recording electrode assembly 48 to determine accurate placement of the catheter 50. These markings 112 can function as placement markers which assist the user in assessing the depth that the catheter 50 is placed within the body 78. For instance, when the recording electrode assembly 48 is located at the distal end 60 of the electronic catheter unit 12 or catheter 50, the markings 112 can be present from the distal end 60 of the catheter 50 to a point 126 on the catheter 50 that spans a distance that can correspond with the average distance between the trachea 92 and nostril 87 in a typical patient. As the catheter 50 is being inserted into the body 78 via the nostril 87, once the markings 112 are no longer visible outside the body 78, the health care provider can be alerted to start monitoring the graphs 37 on the display device 22 to observe the amplitude or impedance versus time plotted from electrical activity data measured by the recording electrode assembly 48 in response to stimulation delivered by the stimulation electrode assembly 46 or to start monitoring for a visual indication, auditory indication, or both that the catheter 50 has be inserted into the correct (e.g., digestive tract) or incorrect location (e.g., respiratory tract). For example, if there is a lack of an evoked potential on an amplitude versus time spectrogram shown on the display device 22 is present once the markings 112 are no longer visible outside the body 78, then the user will be able to determine that the catheter 50 has been improperly inserted into the trachea 92 instead of the esophagus 91, and the catheter 50 should be immediately retracted.

Regardless of the particular method by which proper placement of the catheter 50 is determined, once the distal end or tip 60 of the electronic catheter unit 12 or catheter 50 has been accurately placed within the desired location in the digestive tract, the health care provider can then attach medicine and nutritional delivery tubes to the y-port connector 44 for introducing fluids into the body (e.g., digestive tract) for medical treatment.

Moreover, in conjunction with the stimulation electrode assembly 46 and the recording electrode assembly 48 described herein, the system 2 also contemplates the use of an optional signal generator 58 and associated transceiver 32 that can be used to track the position of the distal end 60 of the catheter 50 as it is being inserted into the patient's body 78. In one embodiment, the signal generator 58, which is located at the distal end 60 of the electronic catheter unit 12 and can be connected to the apparatus 10 via the controller coupler/electrical connected 36 and the wire assembly 62 (see FIGS. 1, 3, and 4), can be formed through a plurality of spirals or coils of wires. Further, the apparatus 10 can be configured to transmit electrical current through the wires such that the current travels in a circular path defined by the coils. This circular motion of current produces an electromagnetic field. In operation, when the apparatus 10 sends electrical current to the coils of the signal generator 58, the coils then transmit a signal or electromagnetic field capable of being detected by the non-invasive transceiver 32. The transceiver 32 then detects the electromagnetic field or signal generated by the signal generator 58 inside the patient's body 78 and the system 2 analyzes the resulting information to cause the display device 22 and the printer 28 to produce additional graphics 37 which can assist the health care provider in a catheter placement procedure in conjunction with electrical activity data acquired by the recording electrode assembly 48. For instance, the system 2 can include a memory device 21 including machine readable instructions and one or more computer programs (which, for example, may include a plurality of algorithms 23) which are used by the processor 20 to process the signal data produced by the signal generator and transmitted by the transceiver 32, after which the processed data is displayed in graphical format on the display device 22 corresponding to the location of the distal end 60 of the catheter 50 within the patient's body 78. In one particular embodiment, the transceiver 32 can be used to determine the distance the signal generator 58 is from the transceiver 32 and its dept in the patient's body 78 can communicate with the display device 22 via the processor 20 to show a reference image of a non-subject body and an image of the signal generator 58 located on the display device 22 with the reference image.

It should also be appreciated that the tubing assembly, electronic catheter unit and catheter position guidance system of the present invention can be used in a variety of catheter procedures and applications. These procedures may involve the treatment of the digestive or gastrointestinal tract or other portions of the human body. These procedures may involve treatment of humans by physicians, physician assistants, nurses or other health care providers. In addition, these procedures may involve treatment of other mammals and animals by veterinarians, researchers and others.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A tubing assembly comprising:
    a catheter having a proximal end and a distal end and extending in a longitudinal direction, wherein the proximal end and the distal end define a lumen therebetween, and wherein the catheter is configured for placement within a digestive tract of a patient including an esophagus;
    a stimulation electrode assembly, wherein the stimulation electrode assembly is configured to deliver an electrical stimulation waveform to tissue at a voltage of from about 1.01volts to about 100 volts and a noise signal over a frequency range, wherein the tissue comprises muscle or cartilage;
    a recording electrode assembly, wherein the recording electrode assembly monitors for electrical activity elicited by the tissue in response to the noise signal and communicates the electrical activity elicited by the tissue to a processor in real-time, wherein the processor is configured to:
        determine if the electrical activity elicited by the tissue is in the form of one or more evoked potentials or corresponds with an impedance signature for the tissue over the frequency range,
        determine whether the catheter is positioned in the esophagus based, at least in part, on the one or more evoked potentials or the determined impedance signature, and
        generate an alert in response to determining that the catheter is not positioned in the esophagus; and
    an electrical connection for delivering the electrical stimulation waveform and noise signal to the stimulation electrode assembly.

2. The tubing assembly of claim 1, wherein the stimulation electrode assembly comprises an anode and a cathode, wherein the anode and the cathode are disposed on an outer wall of the distal end of the catheter.

3. The tubing assembly of claim 1, wherein the stimulation electrode assembly comprises a first electrode disposed on an outer wall of the catheter and a second electrode configured for placement on a surface of skin.

4. The tubing assembly of claim 1, wherein the recording electrode assembly comprises an active recording electrode, an inactive recording electrode, and a reference electrode.

5. The tubing assembly of claim 4, wherein the active recording electrode, the inactive recording electrode, and the reference electrode are disposed on an outer wall of the distal end of the catheter.

6. The tubing assembly of claim 4, wherein the active recording electrode, the inactive recording electrode, and the reference electrode are configured for placement on a surface of skin.

7. The tubing assembly of claim 1, wherein the stimulation electrode assembly is configured for a wired connection or a wireless connection to the processor.

8. The tubing assembly of claim 7, wherein the wired connection comprises a wire or a printed conduit.

9. The tubing assembly of claim 1, wherein the electrical stimulation waveform is a square-wave pulsed waveform.

10. A catheter guidance system configured for placement within a digestive tract of a patient including an esophagus, the catheter guidance system comprising:
    (a) a processor;
    (b) a power source;
    (c) a stimulator; and
    (d) a tubing assembly comprising:
        a catheter having a proximal end and a distal end and extending in a longitudinal direction, wherein the proximal end and the distal end define a lumen therebetween;
        a stimulation electrode assembly, wherein the stimulation electrode assembly is configured to deliver an electrical stimulation waveform to tissue at a voltage of from about 1.01 volts to about 100 volts and a noise signal over a frequency range, wherein the tissue comprises muscle or cartilage; and a recording electrode assembly, wherein the recording electrode assembly monitors for electrical activity elicited by the tissue in response to the noise signal and communicates the electrical activity elicited by the tissue to the processor in real time, the processor being configured to:

determine if the electrical activity elicited by the tissue is in the form of one or more evoked potentials or corresponds with an impedance signature for the tissue over the frequency range, determine whether the catheter is positioned in the esophagus, based, at least in part, on the one or more evoked potentials or the determined impedance signature, and generate an alert in response to determining that (a) the catheter is not placed in the esophagus, or (b) the catheter is correctly placed in a digestive tract of a patient.

11. The catheter guidance system of claim 10, further comprising a display device, wherein the display device is coupled to the processor and displays a graph of the electrical activity elicited by the tissue and communicated to the processor by the recording electrode assembly.

12. The catheter guidance system of claim 10, further comprising a memory device storing instructions which, when executed by the processor, cause the processor to (i) interpret the electrical activity elicited by the tissue and communicated by the recording electrode assembly and (ii) cause the catheter guidance system to alert the user as to correct placement of the catheter in the digestive tract of the patient or alert the user as to incorrect placement of the catheter in the respiratory tract of the patient based on the interpretation of the electrical activity elicited by the tissue.

13. The catheter guidance system of claim 10, wherein the stimulation electrode assembly comprises an anode and a cathode, wherein the anode and the cathode are disposed on an outer wall of the distal end of the catheter.

14. The catheter guidance system of claim 10, wherein the stimulation electrode assembly comprises a first electrode disposed on an outer wall of the catheter and a second electrode configured for placement on a surface of skin.

15. The catheter guidance system of claim 10, wherein the recording electrode assembly comprises an active recording electrode, an inactive recording electrode, and a reference electrode.

16. The catheter guidance system of claim 15, wherein the active recording electrode, the inactive recording electrode, and the reference electrode are disposed on an outer wall of the distal end of the catheter.

17. The catheter guidance system of claim 15, wherein the active recording electrode, the inactive recording electrode, and the reference electrode are configured for placement on a surface of skin.

* * * * *